United States Patent [19]

Sanford-Mifflin et al.

[11] Patent Number: 5,773,219
[45] Date of Patent: Jun. 30, 1998

[54] PROCESS FOR DETECTING ALZHEIMER DISEASE USING CULTURED CELLS

[75] Inventors: Katherine K. Sanford-Mifflin, Dover, Del.; Ram Parshad, Olney; Jay H. Robbins, Potomac, both of Md.

[73] Assignee: The United States of America as represented by the Department of Health and Human Services, Washington, D.C.

[21] Appl. No.: 611,330

[22] Filed: Mar. 8, 1996

Related U.S. Application Data

[63] Continuation-in-part of Ser. No. 228,825, Apr. 18, 1994, abandoned, which is a continuation-in-part of Ser. No. 957,315, Oct. 6, 1992, abandoned.

[51] Int. Cl.$^6$ .............................. C12Q 1/68; C12Q 1/02
[52] U.S. Cl. ................................ 435/6; 435/29
[58] Field of Search .................... 435/6, 29, 34; 424/3; 436/811

[56] References Cited

U.S. PATENT DOCUMENTS 4,933,274  6/1990  Sandford et al. ................ 435/6

OTHER PUBLICATIONS

Parshad R., Cytogenetic Evidence for a Cell Cycle Dependent DNA Repair Deficiency: A Possible Diagnostic Feature of Alzheimer Disease, Proceedings of the 8th International Congress of Human Genetics, American J of Human Genetics Supp 49, 155, Oct. 1991.

Backon J., Dementia in Cancer Patients Undergoing Chemotherapy: Implication of Free Radical Injury and Relevance to Alzheimer Disease, Medical Hypothesis 35 146–147, 1991.

(List continued on next page.)

*Primary Examiner*—Ralph Gitomer
*Attorney, Agent, or Firm*—Morgan & Finnegan

[57] ABSTRACT

A process for aiding in the diagnosis of Alzheimer disease is disclosed in which the frequency of chromatid breaks and gaps is calculated in $G_1$-phase fluorescent-light-irradiated skin fibroblasts or stimulated peripheral blood lymphocytes after the addition of the DNA repair inhibitor caffeine or in $G_2$-phase fluorescent-light-irradiated skin fibroblasts or stimulated peripheral blood lymphocytes after the addition of the DNA repair inhibitor 1β-D-arabinofuranosylcytosine (ara-C). In the $G_1$-phase test, the presence of Alzheimer disease is indicated when the total frequency of breaks and gaps caused by caffeine in the cells being examined is higher than the total frequency caused by caffeine in the normal cells. In the $G_2$-phase test, the presence of Alzheimer disease is indicated when the total frequency of breaks and gaps in the presence of ara-C is much less in the cells being examined than in normal cells.

20 Claims, 2 Drawing Sheets

OTHER PUBLICATIONS

Parshad, R., Price, F. Tarone, R.J. Robbins and Sanford, K.K. (1991) "Cytogenetic evidence for a cell–cycle–dependent DNA repair deficiency: A possible diagnostic feature of Alzheimer Disease." Proceedings of the 8th International Congress of Human Genetics, 6–11 Oct. 1991, Washington, D.C. U.S.A., Am. J. Human Genetics Suppl. 49, 155.

Chen, P., et al., "Heterogeneity in Alzheimer's disease: evidence from cellular radiosensitivity and complementation of this phenotype", Mutation Res. (1991) 256, 21–7.

Tobi, S.E., et al. "Chromosomal radiosensitivity of lymphocytes from Alzheimer's disease patents", J. Med. Genet. (1990) 437–40.

Parshad, R., et al., "Susceptibility to fluorescent light–induced chromatid breaks associated with DNA repair deficiency and malignant transformation in culture", Cancer Res. (1980) 40, 4415–9.

Price, F.M., et al., "Radiation–induced chromatid aberratons in Cockayne syndrome and xeroderma pigmentosum group C fibroblasts in relation to cancer predisposition", Cancer Genet. Cytogenet. (1991) 57, 1–10.

Sanford K.K., et al., "Response of human cells in culture to hydrogen peroxide and related free radicals generated by visible light: relationship to cancer susceptibility", in *Free Radicals, Aging, and Degenerative Diseases*, edited by Johnson, J.E., et al., Alan R. Liss, Inc., New York, 1986, pp. 373–394.

Sanford, K.K., et al., "Role of DNA repair in malignant neoplastic transformation of human mammary epithelial cells in culture", Carcinogenesis (1992) 13, 1137–41.

Parshad, R., et al., "Neoplastic Transformation of human cells in culture associated with deficient repair of light–induced chromosomal DNA damage", Int. J. Cancer: 30, 153–159 (1982).

Parshad, R., et al., "Chromatid damage induced by fluorescent light during $G_2$ phase in normal and Gardner Syndrome fibroblasts," Interpretation in terms of deficient DNA repair, Mutation Research, 151 (1985) 57–63.

Gantt R., et al., "Enhanced $G_2$ chromatid radiosensitivity, an early stage in the neoplastic transformation of human epidermal keratinocytes in culture", Cancer Research 47, 1390–1397 (1987).

Parshad, R., et al., A DNA–Repair Defect In Alzheimer Disease, vol. 42, No. 1, 98A (1994) (Abstracts Submitted to the Annual Meeting of the Western Section of the American Federation for Clinical Research held Feb. 9–12, (1994) (published after filing date of original priority application).

Melnick, L., et al., "Defective DNA Repair In Alzheimer Disease: Use In A Predictive Test On Cultured Cell Lines", Clinical Research vol. 42, No. 3, 464A (Oct. 1994) (published after filing dates of priority applications).

Parshad, R., et al., "Defective DNA Repair In Sporadic, Familial, And Down–Syndrome Alzheimer Disease", Journal of Investigative Medicine, vol. 43 (Supplement 2), 415A (Apr. 1995) (published after filing dates of priority applications).

Melnick, L.K., et al., "Xeroderma Pigmentosum Group–A and Alzheimer Disease Cells Have Similar Defective Repair of Fluorescent Light–Induced DNA Damage", Journal of Investigative Medicine, vol. 43 (Supplement 3), 508A, (Sep. 1995) (published after filing dates of priority applications).

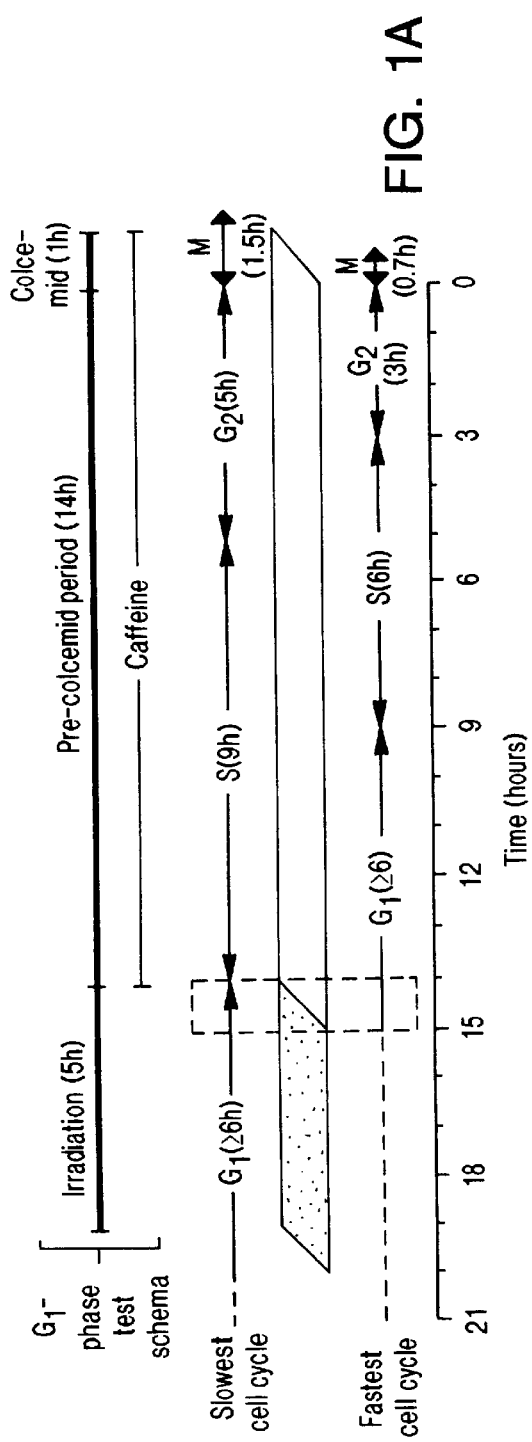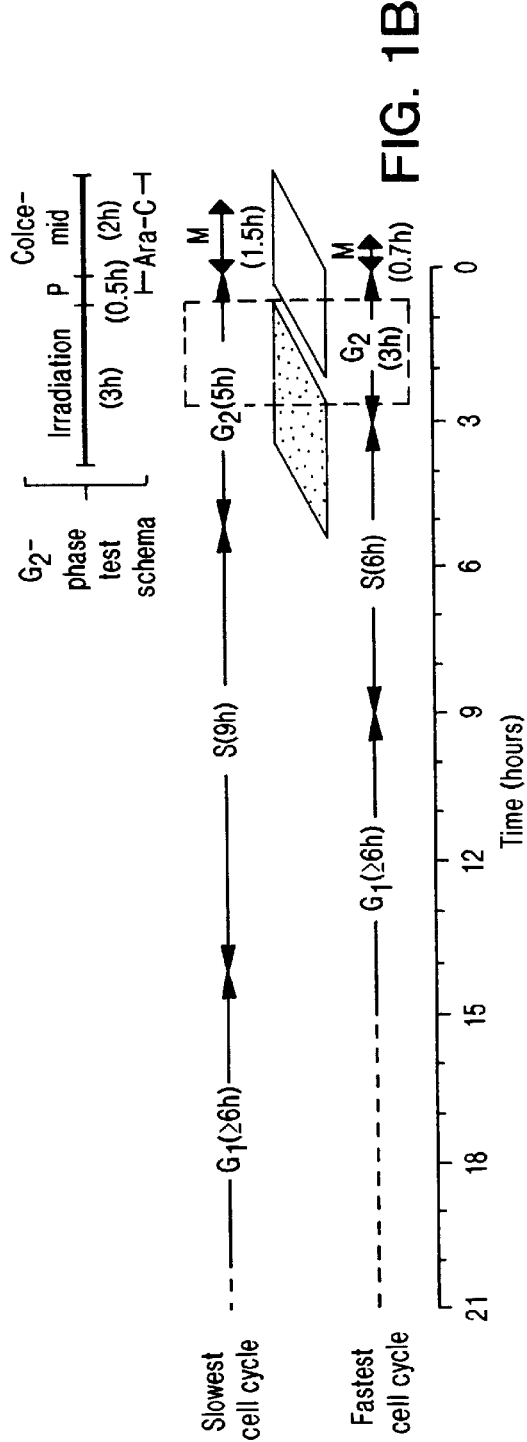

PROCESS FOR DETECTING ALZHEIMER DISEASE USING CULTURED CELLS

This application is a continuation-in-part of U.S. application Ser. No. 08/228,825, filed Apr. 18, 1994 now abandoned, which is a continuation-in-part of U.S. Ser. No. 07/957,315, filed Oct. 6, 1992 now abandoned.

FIELD OF THE INVENTION

The invention relates to a process which distinguishes between clinically normal individuals and those who have or are destined to develop Alzheimer disease (AD). The invention relates to methods of screening for (e.g., detecting or diagnosing or indicating the presence of) AD in a human subject. The invention also relates to methods of aiding or assisting in the diagnosis of AD in a human subject. The process is based on the cytogenetic response of an individual's cultured cells to fluorescent light in the presence and absence of a DNA repair inhibitor during the post-exposure period. It encompasses two tests: the $G_1$-phase test, which is applicable to skin fibroblasts and peripheral blood lymphocytes, and the $G_2$-phase test, which is also applicable to skin fibroblasts and peripheral blood lymphocytes.

BACKGROUND OF THE INVENTION

The gene for only a small number of familial cases of AD appears to have been discovered. A mutation in the β-amyloid gene located on chromosome 21 has been found in a small number of early-onset patients who have familial AD. However, over 90% of the cases of familial AD and possibly 100% of the cases of sporadic AD do not have any known mutation in the β-amyloid gene. Furthermore, the majority of AD families show no evidence of linkage to markers on chromosome 21 and, therefore, the chromosomal localization of the gene(s) responsible for the vast majority of AD cases, particularly the late-onset form, is not likely to be on chromosome 21. Nevertheless, it is likely that all cases of AD may be due to abnormalities in the metabolism of β-amyloid. Thus, in addition to the few families with the mutation in the β-amyloid gene, it is known that all DS patients with trisomy 21 eventually develop AD. Since all patients with AD have a basically similar neuropathologic picture of amyloid plaques, it is likely that AD is caused by mutations which affect the transcription or expression of the β-amyloid gene or which affect subsequent metabolism of β-amyloid.

One of the most promising methods for chromosomal localization of disease-causing genes is restriction fragment length polymorphism linkage analysis. These studies have been applied in the search for the familial AD gene(s). The first such study reported a chromosome 21 localization of the AD gene based on pooled results from four familial AD families referred to as the Canadian, Italian, German, and Russian kindreds. Subsequently, it was reported that linkage studies indicate that the AD gene was not the β-amyloid gene, and it now appears that in at least three of the four families the AD gene may not even be located on chromosome 21.

The greatest obstacle to the successful chromosomal localization of the AD gene in any single family is the lack of sufficient numbers of persons from whom blood samples are obtainable (for the propagation in lymphoblasts of the DNA needed for analysis) and for whom the presence or absence of the AD gene is known. For example, in the Canadian AD family, only 8 persons from whom blood cells have been obtained are known to be affected with AD. Blood cells are also available from several other family members who are past the age at which AD symptoms would have been noted if the members had inherited the gene (i.e., 'escapees'). However, in no single family are blood cells from sufficient numbers of affected and escapees available to permit the chromosomal localization of the AD gene. Blood cells from sufficient numbers of informative individuals would be available, however, if the presence or absence of the AD gene could be ascertained in the scores of family members who are at-risk for AD and whose blood cells have already been cultured or could readily be obtained. For example, in the German family, approximately 150 young, asymptomatic persons are at-risk for the disease, but their DNA can not be used in the linkage analysis until their possible carrier status is resolved as they age over several decades. A test which, for whatever reason, would clearly indicate which of these at-risk persons had inherited the gene might immediately make it possible for the restriction fragment length polymorphism linkage studies to be successfully completed.

From studies of the rare human disease xeroderma pigmentosum (XP), it was postulated that DNA repair is required to maintain the integrity of the nervous system by preventing primary neuronal degeneration due to unrepaired DNA damaged by endogenous UV-mimetic metabolites (see, e.g., Robbins, et al., "Xeroderma pigmentosum: an inherited disease with sun sensitivity, multiple cutaneous neoplasms, and abnormal DNA repair", Ann. Intern. Med. (1974) 80, 221–48; Andrews, A. D., et al., "Xeroderma pigmentosum neurological abnormalities correlate with colony-forming ability after ultraviolet radiation", Proc. Natl. Acad. Sci. USA (1978) 78, 1984–8; Robbins, J. H., et al., "Neurological disease in xeroderma pigmentosum: documentation of a late onset type of the juvenile onset form", Brain (1991) 114, 1335–61). The finding that ataxia telangiectasia patients, all of whom suffer from a primary neuronal degeneration, have a marked hypersensitivity to the lethal effects of ionizing radiation (see, e.g., Taylor, A. M. R., et al., "Ataxia-telangiectasia: a human mutation with abnormal radiation sensitivity", Nature (1975) 258, 427–9) suggested that their neurodegeneration might also be due to defects in the repair of neuronal DNA damaged by endogenous radiomimetic metabolites. It was therefore suggested that other primary neuronal degenerations might also be associated with hypersensitivity to ionizing radiation (hypersensitivity to ultraviolet radiation (UV) being unlikely in the absence of sunlight sensitivity in these patients in vivo). Subsequently, hypersensitivity to X-rays and/or to the alkylating agent N-methyl-N'-nitro-N-nitrosoguanidine (MNNG) was demonstrated in cultured cells from patients with the following neurodegenerations: AD, Huntington disease, Parkinson disease, familial dysautonomia (Riley-Day syndrome), idiopathic orthostatic hypotension, multiple system atrophy, Down syndrome, Usher syndrome, and autosomal recessive retinitis pigmentosa. (See, e.g., Moshell, A. N., et al., "Radiosensitivity in Huntington's disease: implications for pathogenesis and presymptomatic diagnosis", Lancet (1980) 1, 9–11; Scudiero, D. A., et al., Proc. Natl. Acad. Sci. USA (1981) 78, 6451–5; Scudiero, D. A., et al., "Alzheimer disease fibroblasts are hypersensitive to the lethal effects of a DNA-damaging chemical", Mutation Res. (1986) 159, 125–31; Robbins, J. H., et al., "Parkinson's disease and Alzheimer's disease: hypersensitivity to X-rays in cultured cell lines", J. Neurol. Neurosurg. Psychiatry (1985) 48, 916–23; Otsuka, F., et al., "Hypersensitivity to ionizing radiation in cultured cells from Down syndrome patients", J. Neurol. Sci. (1985) 69, 103–12; and Nove, J., et al., "Radiation sensitivity of fibroblast strains from patients with Usher's syndrome, Duchenne muscular dystrophy, and Huntington's disease", Mutation Res. (1987) 184, 29–38). Radiosensitivity in Friedreich's ataxia and alkylation hypersensitivity in amyotrophic lateral sclerosis have also been demonstrated (see, e.g., Chamberlain, S. and Lewis, P. D., "Studies of cellular hypersensitivity to ionizing radiation in Friedreich's ataxia", J. Neurol. Neurosurg. Psychiatry (1982) 45, 1136–8 and Bradley, W. G., et al., "Deficient repair of alkylation damage of DNA in Alzheimer's disease and amyotrophic lateral sclerosis cells", in Cosi, V. et al., editors: *Amyotrophic Lateral Sclerosis*, Plenum Press, Milan, pp. 3–6, 1985, respectively). The radiosensitivity which was found in Huntington disease has been confirmed by others (see, e.g, Chen, P., et al., "Huntington's disease: implications of associated cellular radiosensitivity", Clin. Genet. (1981) 20, 331–6; McGovern, D. and Webb, T., "Sensitivity to ionizing radiation of lymphocytes from Huntington's chorea patients compared to controls", J. Med. Genet. (1982) 19, 168–74). In none of these diseases were the cells found to be hypersensitive to UV, thereby demonstrating a specificity of the hypersensitivity for ionizing radiation.

In previous studies on AD, cells from patients with familial or sporadic AD were tested and found to have a hypersensitivity to the lethal effects of ionizing radiation, as determined by the try pan-blue dye-exclusion assay using lymphoblasts, and of MNNG, as determined by colony-forming ability of fibroblast strains. Finding AD cells to be hypersensitive was somewhat unexpected, because the AD brain has a different histopathology from that of the other primary neurodegenerations. However, these findings have been confirmed by several investigators. Robison et al. and Jones et al., using primarily the alkaline elution technique for detecting repair of DNA-strand breaks, have shown hypersensitivity to methylmethane sulfonate (MMS) and to MNNG in cells from both familial and sporadic AD patients. (See Robison, S. H., et al., "Alzheimer's disease cells exhibit defective repair of alkylating agent-induced DNA damage", Ann. Neurol. (1987) 21, 250–8 and Jones S. K., et al., "Decreased DNA repair in familial Alzheimer's disease", Mutation Res. (1989) 219, 247–255). Boerrigter et al., also using the alkaline elution assay, found that peripheral blood lymphocytes from familial AD patients had hypersensitivity to N-ethyl-N-nitrosourea but that lymphocytes from sporadic AD patients did not (see Boerrigter, M. E. T. I., et al., "Decreased DNA repair capacity in familial, but not in sporadic Alzheimer's disease", Neurobiol. Aging (1991) 12, 367–70). Li and Kaminskas, using the alkaline elution assay, reported hypersensitivity of AD fibroblasts to MNNG (see Li, J. C. and Kaminskas, E., "Deficient repair of DNA lesions in Alzheimer's disease", Biochem, Biophys. Res. Commun. (1985) 129, 733–8). However, one of the inventors (JHR), using the alkaline elution assay, but growing and treating the AD fibroblasts in his usual manner, which is different from that of these other investigators, were not able to show such hypersensitivity to MNNG or MMS, indicating that the experimental conditions may be critical. (See Kinsella T. J., et al., "Alzheimer's disease fibroblasts have normal repair of N-methyl-N'-nitro-N-nitrosoguanidine-induced DNA damage determined by the alkaline elution technique", Biochem, Biophys. Res. Commun. (1987) 149, 355–61 and Kinsella. T. J., et al., "Alzheimer's disease fibroblasts have normal repair of methylmethane sulfonate-induced DNA damage determined by the alkaline elution technique", Neurol. (1987) 37 (Suppl. 1), 166, respectively). Finally, Chen et al. just recently confirmed the inventors' ionizing-radiation survival experiments by showing that lymphoblasts from 12 of 14 Australian patients with the clinical diagnosis of sporadic AD (which diagnosis by their staff is not confirmed by autopsy 10% of the time) were hypersensitive to the lethal effects of ionizing radiation (as tested by colony-forming ability in agar) and showed an average two-fold increased frequency of ionizing-radiation-induced chromosomal aberrations compared to the 14 normal lines (see Chen, P., et al., "Heterogeneity in Alzheimer's disease: evidence from cellular radiosensitivity and complementation of this phenotype", Mutation Res. (1991) 256, 21–7). Tobi et al. have also shown an increased number of chromosomal aberrations in ionizing-radiation-treated PHA-stimulated peripheral blood lymphocytes from sporadic AD patients (see Tobi, S. E., et al., "Chromosomal radiosensitivity of lymphocytes from Alzheimer's disease patients", J. Med. Genet. (1990) 437–40).

Unfortunately, none of the previously mentioned tests provides large enough differences between normal and AD cells to be useful in reliably distinguishing an individual AD patient from normal. The inventors, therefore, searched for a distinguishing test which would be useful and found that the $G_1$- and $G_2$-tests of the present invention gave very large differences in distinguishing AD from normal cells.

The $G_2$-phase test is the subject of U.S. Pat. No. 4,933,274, issued to Sanford, K. K., Parshad, R., Jones, G. M. and entitled "Process for Detecting Genetic Susceptibility to Cancer". This patent describes a $G_2$-phase test using either X-rays or fluorescent light to damage fibroblasts or peripheral blood lymphocytes for distinguishing cells of individuals susceptible to cancer from cells of normal individuals. The teachings of this patent are hereby incorporated by reference herein.

It should be noted that the present invention uses fluorescent light to irradiate the cells in both the $G_1$- and G2-phase tests. Ionizing radiation (e.g., X-rays) is not used in the $G_1$-phase test of the present invention because X-rays produce a mitotic block in the early $G_2$ phase, thereby perturbing the cell cycle and interfering with the test, for the cells irradiated in $G_1$ phase must subsequently progress through S-phase, the $G_2$-phase, and into mitosis in an appropriate time in order to be harvested. It should also be noted that ionizing radiation (e.g. x-rays) is also not used in the $G_2$ phase test of the present invention since AD cells give normal results in the $G_2$-phase test if the cells are irradiated with X-rays instead of with fluorescent light.

The processes of the present invention differ from the known technologies described above for distinguishing AD from normal cells in several important respects: 1) the cells are irradiated with cool-white fluorescent light, rather than with ionizing radiation; 2) after irradiation, chemicals which inhibit DNA repair (caffeine for the $G_1$-phase test and ara-C for the $G_2$-phase test) are added to the cultures; 3) the experiments are conducted so that the metaphase cells are in a known phase of the cell cycle at the time of irradiation (e.g., in the $G_1$-phase for the caffeine experiments and in the $G_2$-phase for the ara-C experiments) rather than in just the $G_0$ phase or in several phases (the irradiation protocols for $G_1$ and $G_2$ phase tests are based on the observation that different cell lines grown under constant conditions at 37° C. have a variable $G_1$ period but relatively constant periods of $G_2$ (2–5 h), S (6–9 h), and M (½–1 h)); 4) chromatid damage is quantified (measured as the sum of the frequencies of chromatid breaks and chromatid gaps) instead of quantifying any chromosomal aberrations (e.g., chromosome breaks, dicentrics, fragments, and interchanges).

The present invention is expected to lead to several contributions related to AD. Among these contributions are the following: 1) the invention should aid considerably in the diagnosis of suspected AD (which affects or will affect several million Americans) by providing a test which detects the presence of AD before signs and symptoms become fully apparent; 2) in familial AD families the invention will make it possible to determine the presence or absence of the AD gene(s) in persons at risk for AD long before the persons have any signs or symptoms of the disease; such presymptomatic diagnosis is expected to be of value to the persons at risk, for they could then, for example, make rational plans for their future, including participating in medical treatments or protocols designed to slow, alleviate, or prevent altogether the neurodegeneration of AD; 3) in familial AD families, identifying which at-risk persons carry the gene(s) for AD will make it possible for restriction-fragment-length-polymorphism and other linkage studies to determine the chromosomal localization and, eventually, the exact site, identification, and cloning of the AD gene(s); 4) the abnormal frequencies of chromatid breaks and gaps (which reflect defective DNA repair processes) which the present invention reveals in AD cells will make it possible to study and understand how defective DNA repair is involved in the cause and/or pathophysiology of AD, and may lead to methods to delay or prevent the clinical onset of AD.

The present invention is an improvement over the closest known technologies in that it provides a much greater difference between the response of AD and normal cells. This greater difference makes it possible to distinguish a single AD cell line (i.e., a cell line from one AD patient) from lines from most, if not all, normal people.

SUMMARY OF THE INVENTION

It is an object of the invention to distinguish clinically normal individuals and those who have a non-AD dementia from those who have or are destined to have AD.

As mentioned above, the invention relates to methods of screening for (e.g., detecting or diagnosing or indicating the presence of) AD in a human subject. The invention also relates to methods of aiding or assisting in the diagnosis of AD in a human subject. If the association of the results in the methods of the present invention with the ultimate neuropathological definitive diagnosis of the presence or absence of AD is strong enough, the methods of the present invention may, in themselves, be sufficient to distinguish a person with AD from a normal person or a person with some other form of dementia. In any event, when used either alone or in conjunction with other tests, the methods of the invention will improve the probability of correctly diagnosing the presence or absence of AD.

The present invention provides assays for detecting AD or the predisposition or susceptibility to AD. The invention comprises assay and kits formed therewith, with which to test for AD or AD susceptibility by statistical comparison of chromatid break and gap frequency arising in skin fibroblasts or peripheral blood lymphocytes in the $G_1$-phase test or skin fibroblasts or peripheral blood lymphocytes in the $G_2$-phase test, with that occurring in comparably-treated normal cells.

The present invention is based on the cytogenetic response of an individual's cultured cells to fluorescent light in the presence or absence of a DNA repair inhibitor during the post-exposure period. The present invention includes two novel processes for evaluating cytogenetically DNA repair capacities which distinguish cultured normal cells from AD cells. Both of these processes involve the damaging of cultured cells' DNA with cool-white fluorescent light, followed by addition to the cultures of a chemical which blocks DNA-repair processes. The effect of the chemical is then calculated by subtracting the amount of chromatid damage observed in the absence of a chemical from that in its presence. In the absence of either of these chemicals, no differences are found between normal cells and cells of people who either have AD, are destined to develop AD, or at risk to develop AD.

Thus, the invention relates to methods for detecting AD or susceptibility to AD comprising irradiating $G_1$-phase cell lines derived from patients, adding a DNA repair inhibitor such as caffeine to a portion of the cell cultures, and detecting and analyzing the chromatid damage (the "$G_1$-phase test").

The invention also relates to the methods for detecting AD or susceptibility to AD comprising irradiating $G_2$-phase cell lines derived from patients, adding a DNA repair inhibitor such as ara-C to approximately half the cell cultures, and detecting and analyzing the chromatid damage (the "$G_2$-phase test").

The "$G_1$-phase test" of the invention relates to a process for aiding in the diagnosis of Alzheimer disease in a patient suspected of having Alzheimer disease comprising
  a) obtaining cells from the patient;
  b) culturing the cells to obtain cell cultures wherein $G_1$-phase cells are present;
  c) irradiating with fluorescent light the cell cultures wherein $G_1$-phase cells are present to obtain irradiated cell cultures;
  d) adding caffeine to approximately half of the irradiated cell cultures;
  e) incubating the irradiated cell cultures to allow for DNA repair;
  f) arresting cell division in the irradiated cell cultures;
  g) counting the chromatid breaks and chromatid gaps to determine chromatid damage in the irradiated cell cultures to which caffeine was added;
  h) counting the chromatid breaks and chromatid gaps to determine chromatid damage in the irradiated cell cultures to which caffeine was not added;
  i) subtracting from the amount of chromatid damage observed in the irradiated cell cultures to which caffeine was added the amount of chromatid damage observed in the irradiated cell cultures to which caffeine was not added to obtain a numerical result; and
  j) determining whether the numerical result indicates that a significant increase in the amount of chromatid damage is observed in the irradiated cell cultures to which caffeine was added as compared to the amount of chromatid damage observed in the irradiated cell cultures to which caffeine was not added; wherein the presence of a significant increase indicates the presence of Alzheimer disease in patients suspected of having Alzheimer disease.

The "$G_2$-phase test" of the invention relates to a process for aiding in the diagnosis of Alzheimer disease in a patient suspected of having Alzheimer disease comprising the steps of:
  a) obtaining cells from the patient;
  b) culturing the cells to obtain cell cultures wherein $G_2$-phase cells are present;
  c) irradiating with fluorescent light the cell cultures wherein $G_2$-phase cells are present to obtain irradiated cell cultures;

d) adding ara-C to approximately half of the irradiated cell cultures;

e) incubating the irradiated cell cultures to allow for DNA repair;

f) arresting cell division in the irradiated cell cultures;

g) counting the chromatid breaks and chromatid gaps to determine chromatid damage in the irradiated cell cultures to which ara-C was added;

h) counting the chromatid breaks and chromatid gaps to determine chromatid damage in the irradiated cell cultures to which ara-C was not added;

i) subtracting from the amount of chromatid damage observed in the irradiated cell cultures to which ara-C was added the amount of chromatid damage observed in the irradiated cell cultures to which ara-C was not added to obtain a numerical result; and j) determining whether the numerical result indicates that a significant increase in the amount of chromatid damage is observed in the irradiated cell cultures to which ara-C was added as compared to the amount of chromatid damage observed in the irradiated cell cultures to which ara-C was not added;

wherein the absence of a significant increase of at least 15 gaps plus breaks per 100 metaphase cells indicates the presence of Alzheimer disease in patients who are suspected of having Alzheimer disease.

BRIEF DESCRIPTION OF THE DRAWINGS

FIG. 1. Test schemas and their relation to the cell cycle. A. The $G_1$ test. B. The $G_2$ test.

DETAILED DESCRIPTION OF THE INVENTION

Figure 2:
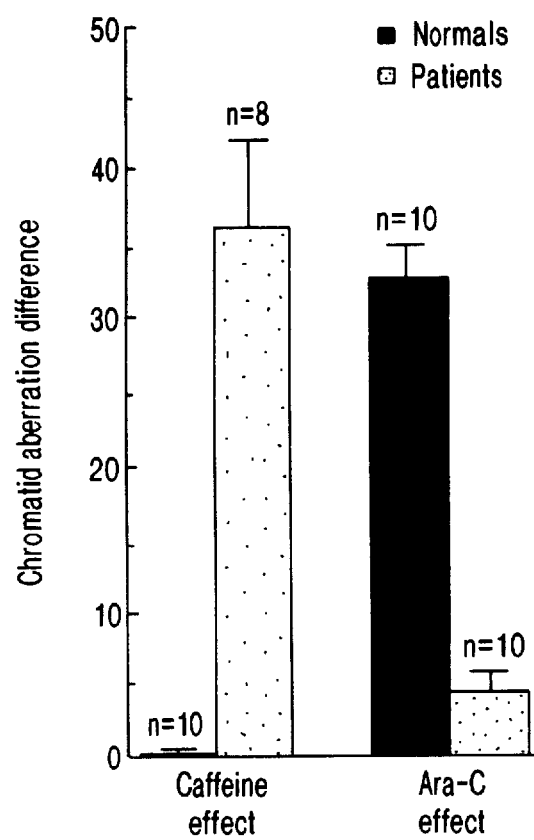
FIG. 2. Caffeine and ara-C expose a DNA-repair defect in fluorescent light-irradiated fibroblast lines from patients with, or with impending, neuropathology of AD.

Exposure of human cells in culture to fluorescent light produces several DNA lesions, including strand breaks and base damage. The breaks, together with indirect breaks formed during repair of base damage, are quantified as chromatid breaks and gaps at the subsequent metaphase. When exposed during $G_1$ phase, skin fibroblasts from patients with AD have similar frequencies of chromatid aberrations (CA) as fibroblasts from age-matched normal donors. However, addition of caffeine during the S-phase following $G_1$ light exposure significantly increases frequencies of CA only in cells of people who either have AD, are destined to develop AD, or are at risk to develop AD. Without being bound by theory, these results suggest that damage is repaired in normal cells during G, phase but persists in cells of people who either have AD, are destined to develop AD, or are at risk to develop AD. During S phase, the unrepaired lesions cause spaces to form in newly synthesized DNA and these spaces are kept open when caffeine is present. Addition of ara-C, an inhibitor of DNA repair synthesis, to cells after $G_2$ light exposure significantly increases CA in the normal cells, but not the cells of people who either have AD, are destined to develop AD, or are at risk to develop AD, indicating that normal but not AD or AD susceptible cells have incision activity for removal of base damage during $G_2$. From these results it is inferred that lesions persist in cells of people who either have AD, are destined to develop AD, or are at risk to develop AD during $G_1$ and G2 and that the premature death of postmitotic neurons in AD may be caused by accumulation of unrepaired DNA lesions. The abnormal cytogenetic responses of cells of people who either have AD, are destined to develop AD, or are at risk to develop AD provide the basis for the tests of the present invention.

It is anticipated that any chemical which inhibits repair during S-phase, i.e., which inhibits post-replication repair, can act as a substitute for caffeine in the $G_1$-phase test. It is also anticipated that any chemical which inhibits DNA repair during $G_2$, i.e., which inhibits DNA repair synthesis and/or DNA ligation during $G_2$-phase, can act as a substitute for ara-C in the $G_2$-phase test. Thus, the invention relates to methods for detecting AD or susceptibility to AD comprising irradiating $G_1$-phase cell lines derived from patients, adding a DNA repair inhibitor such as caffeine to a portion of the cell cultures, and detecting and analyzing the chromatid damage (the "$G_1$-phase test"). The invention also relates to the methods for detecting AD or susceptibility to AD comprising irradiating G2 - phase cell lines derived from patients, adding a DNA repair inhibitor such as ara-C to approximately half the cell cultures, and detecting and analyzing the DNA damage (the "$G_2$-phase test").

To ensure accuracy and reproducibility of results in the present process, various process parameters merit particular consideration and control samples should always be run. The parameters include: pH, temperature, cell density, culture medium or serum, microbial contamination and visible light exposure (effective wavelength 405 nm). These are each discussed in U.S. Pat. No. 4,933,274, which is incorporated by reference herein.

The following examples are exemplary of the present processes and incorporate suitable process parameters for use herein. These parameters may be varied, however, and the following should not be deemed limiting.

The following exemplary protocols are performed in parallel with test samples and control cultures.

MATERIALS AND METHODS

Source of Cells. Cultures of skin fibroblasts developed from biopsy material as described for example by Goetz, I. E. "Growth of human skin fibroblasts from punch biopsies". TCA Manual, 1:13–15 (1975), Tissue Culture Methods and Applications, P. F. Kruse, Jr. and M. K. Patterson, Jr. Eds., Academic Press, New York, (1973) and established cell lines obtained from cell repositories such as the American Type Culture Collection, 12301 Parklawn Drive, Rockville, Md. 20852 or NIGMS Human Genetic Mutant Cell Repository, Coriell Institute of Medical Research, 401 Haddon Avenue, Camden, N.J. 08103 may be used. For instance, in the examples described below various lines of skin fibroblasts were obtained from the NIGMS Human Genetic Mutant Cell Repository (GM) and the NIH Aging Cell Repository (AG).

Quantification of Chromatid Damage. To quantify chromatid damages in both the test and control samples, 50 to 100 metaphase cells from each culture are examined for chromatid breaks and gaps. Chromatid interchanges generally do not occur for they arise infrequently in human fibroblasts. Breaks appear as chromatid discontinuities with displacement of the broken segment, while gaps (non-staining regions) show no displacement of the segment distal to the lesion. Gaps are scored only if they are longer than the chromatid width (See, ISCN: An International System for Human Cytogenetic Nomenclature. Cytogenet. Cell Genet., 21:309–404 (1978). Cells in prometaphase or metaphase cells with understained or overstained chromosomes are not considered suitable for analysis because understained chromosomes could have unstained gap-like regions, while overstaining could obscure gaps.

Statistical Calculations. In all cases, statistical comparisons of data are based on the t-test after taking a square root transformation of the aberration frequencies (Snedecor et al. Statistical Methods, pp. 208–213 Ames, IA:University Press (1980)).

FIG. 1 shows test schemas and their relation to the cell cycle. Only the subpopulation of metaphase cells in the cultures, arrested by colcemid, were scored in the assay. The time lines for the fastest and slowest cell cycles show where the metaphase cells were in the cell cycle during the treatments. The dashed lines indicate $G_1$ phases that are longer than six hours. The dashed rectangle indicates where in their cell cycle the metaphase cells had been when irradiation ended. The shaded parallelogram indicates where, relative to the cell cycle, the arrested cells had been during their irradiation. The unshaded parallelogram indicates where, relative to the cell cycle, the metaphase cells had been during their exposure to the DNA-repair inhibitor. FIG. 1 (A) shows a G1-phase test schema. The slowest cycling metaphase cells would likely have received all their irradiation in $G_2$ phase ($G_2$); the fastest might have received some irradiation in the prior mitosis (M), prior $G_2$ phase ($G_2$), and even last part of the prior synthesis phase (S). Each arrested cell would have been exposed to caffeine during its entire S which followed irradiation. FIG. 1 (B) shows a typical $G_2$-phase test schema. Details are as above. The slowest cycling metaphase cells would have received all or almost all their irradiation in $G_2$; the fastest would have received at least some irradiation also in S. Each metaphase cell would have been exposed to 1-B-D-arabinofuranosylcytosine (ara-C) during at least part of its $G_2$ but never in S. P, pre-colcemid period.

In the experiments described in the examples herein at least 28 of 31 normal donors and 10 of 11 donors with non-amyloid neurodegenerations gave normal results in the tests of the invention. Cells from all 12 DS, 11 sporadic AD, and 16 familial AD patients tested, as did XP-A cells, had abnormal ara-C and/or caffeine test results. In 1 of our 4 AD families, an abnormal caffeine test result was found in all 10 afflicted individuals (including 3 who were asymptomatic when their skin biopsies were obtained) and in 8 of 11 offspring at a 50% risk for AD.

EXAMPLE 1

$G_1$-Phase Test

The $G_1$ test (FIG. 1A) was designed to detect the consequences of DNA damage left unrepaired in $G_1$. Briefly, in the $G_1$-phase test, the cells were irradiated with fluorescent light for 5 hours, 14 hours after which colcemid was added for 1 hour to arrest cells in metaphase. Thus, all metaphase cells examined had been in $G_1$ at the end of irradiation (see dashed rectangle, FIG. 1A). Lesions not repaired in $G_1$ would persist into S phase. If these lesions inhibited DNA replication, they could result in discontinuities (i.e., gaps) in newly synthesized DNA observable as chromatid aberrations in the succeeding metaphase. These discontinuities are normally mended during S phase by a daughter-strand, postreplication repair process which can be blocked by caffeine. Therefore, to retain such discontinuities, half the cultures were exposed to caffeine from the end of irradiation through S and into $G_2$ (as indicated by the unshaded parallelogram, FIG. 1A).

$G_1$-Phase Test For Fibroblasts

A detailed protocol for quantifying the response of fibroblasts to $G_1$-phase irradiation is set forth below:

1. Log-phase skin fibroblasts are prepared by:
   (a) Transferring cells to T-25 flasks 11 days before assaying.
   (b) Renewing the culture medium on days 8 and 6 before assay. One medium found suitable for use is Dulbecco's Modified Eagle's medium ("DMEM"—Morton, H. C. "A survey of commercially available tissue culture media", In Vitro 6:89–108 (1970)), a chemical nutrient solution designed for growing cells in culture, with 4.5 g/l glucose and 10% fetal bovine serum (Bio Whitaker, Walkersville, Md. & ICN Biomedical, Inc., Costa Mesa, Calif., respectively).
   (c) Subculturing the fibroblasts on day 4 before assay.
   (d) Renewing the culture medium 24 hours before assay. Cultures should be subconfluent for assay.
2. To prepare replicate cultures for irradiation:
   (a) Rinse culture with EDTA (ethylene diamine tetraacetic acid) (versene 1:5000, Bio Whitaker) for about 30 seconds.
   (b) Withdraw versene and add just enough trypsin-EDTA solution to cover cell monolayer. The trypsin-EDTA solution is prepared just prior to use by diluting 1:10 with the EDTA solution a frozen stock (1% Worthington 3× crystallized trypsin in 0.1% EDTA in Dulbecco's PBS without CA++ or Mg++) resulting in a final trypsin concentration of 0.1%.
   (c) Gently tap flask to detach cells, then inactivate trypsin by adding a small aliquot of serum-supplemented culture medium. Bottles of medium and serum at the commercial source of preparation, during shipping, storage and use, as well as cultures in the medium, should at all times be protected from light of wavelength<500 nm to avoid adversely affecting the assay results. Suggested means include aluminum foil wraps, yellow bags, gold or red room lights, and appropriate light filters for microscope observation.
   (d) Adjust cell suspension to about $0.5-\times10^5$ cells/2 ml medium. For reproducibility, inoculum size should be adjusted to obtain equivalent cell densities (e.g. 75% confluence) at the time of irradiation 48 hours later.
   (e) Inoculate cell suspensions into Leighton tubes, each containing a 9×50 mm coverslip (No. 1 thickness Bellco Glass Co., Vineland, N.J.). For best results, equilibrate gas phase with humidified 10% $CO_2$ in air, seal with #0 silicone stopper and incubate at 37° C. It should be noted that maintenance of physiologic pH is necessary to avoid adversely affecting test results.
   (f) Alternatively, log-phase skin fibroblasts can be inoculated into T-25 flasks at a cell density to yield a semi-confluent cell sheet after 48 h incubation.
   (g) Renew medium 24 hours before irradiation.
3. To irradiate cultures:
   (a) Expose cultures of cells from normal and presumed AD patients for 5 h to fluorescent light at 37° C. The light source can be a desk lamp fitted with a cool-white 15-W fluorescent Westinghouse bulb (F15 T8-CW). Cultures are exposed at a distance to yield an intensity of 5 $W/m^2$ at the growth surface as measured by an 1L 700 research radiometer (International Light Inc., Dexter Industrial Green, Newburyport, Mass.). Control unirradiated cultures are handled identically but shielded from light.
   (b) Add caffeine (0.25 mM, Sigma) to approximately half of the irradiated cultures; incubate for an additional 15 h completely shielded from light.

(c) Add colcemid (0.1 ug/ml, Gibco, Grand Island, N.Y.) to all cultures during the last hour.

4. To process cells for chromosome analysis:
   (a) After about 1 hour incubation with Colcemid (N-desacetyl-N-methylcochicine) at 37° C., decant medium, invert culture and gently add to roof of culture vessel 2 to 5 ml 0.53% KCl in distilled $H_2O$ prewarmed to 37° C. Return culture to original position and incubate for 15 minutes at 37° C. Alternatively, cells can be removed with trypsin from the T-25 flasks and processed in suspension as described later for lymphocytes.
   (b) Prepare fixative at room temperature just before use. A suitable fixative comprises 1 part glacial acetic acid:3 parts absolute methanol.
   (c) Decant KCl solution, invert culture and gently add to roof of the culture vessel 2 to 5 ml fixative. Return culture to original position and fix for about 30 minutes at room temperature.
   (d) Remove coverslip from vessel, air-dry at an angle and, preferably, store for at least 24 hours before staining.
   (e) Stain coverslip about 4 minutes with aqueous Wright-Giemsa (3 parts) plus distilled water (125 parts) (Harleco, Gibbstown, N.J.). Rinse in tap water, air dry, dip in xylene and mount on a clean slide with a mounting medium.

5. To quantify chromatid aberrations:
   (a) Scan samples for complete well-spread metaphase cells.
   (b) Score each metaphase cell for number of chromatid breaks (showing distinct dislocation and misalignment of the chromatid fragment), chromatid gaps (or achromatic lesions longer than the width of the chromatid, showing apparent chromatid discontinuity, but no dislocation), and other chromosomal abnormalities as experimental objectives dictate.

6. Determine caffeine effect (see table 1).

$G_1$-Phase Test For Peripheral Blood Lymphocytes

To quantify the response of peripheral blood lymphocytes to Gl-phase irradiation, lymphocytes are prepared as described in steps 1–10 in Example 2 below and are tested in the $G_1$-phase test as described in steps 3–6 immediately above, except that step 8 in Example 2 below is conducted at 48 h instead of at 72 h, and in step 3(b), above, 2 mM caffeine is used instead of 0.25 mM and the cell cultures are incubated for 18 hours instead of 15 hours after the addition of caffeine and before the addition of colcemid.

EXAMPLE 2

$G_2$-phase test

The $G_2$ test (FIG. 1B), in which nucleotide excision repair is blocked by ara-C, was designed to measure directly the extent of the incision step of excision repair in normal and patient cells. In nucleotide excision repair the damaged DNA strand is enzymatically incised, after which the damaged and some neighboring nucleotides are removed. The resulting space is filled in by a DNA polymerase whose action can be inhibited by ara-C. Such inhibition results in an unligatable segment of DNA, which can then lead to a chromatid aberration in the succeeding metaphase. Briefly, in the $G_2$ test the cells were irradiated with fluorescent light for 2 to 3 hours, followed shortly by addition of colcemid to arrest cells in metaphase, so that all metaphase cells examined would have been in $G_2$ by the end of irradiation (see dashed rectangle, FIG. 1B). Furthermore, ara-C was added to half the cultures just 10 min. after the end of irradiation. Thus, all these metaphase cells examined would have been exposed to ara-C during at least some portion of their $G_2$ (indicated by the unshaded parallelogram, FIG. 1B).

A detailed protocol for quantifying the response of fibroblasts and peripheral blood lymphocytes to $G_2$-phase irradiation is set forth below:

Skin Fibroblasts

1. To test for repair of damage inflicted during $G_2$-phase, cells grown on coverslips in Leighton tubes or in T-25 flasks are exposed for 3 h at 37° C. to cool-white fluorescent light ($8W/m^2$ at the growth surface). For light source, see $G_1$ test but use two light bulbs.
2. Add the DNA repair inhibitor, 1β-D-arabinofuranosylcytosine (ara-C, 50 μM, Sigma) to approximately half the cultures at 10 min after light exposure and colcemid (0.1 μg/ml) to all cultures at 30 min postexposure for 2h. 3. Process for chromosome analysis as in $G_1$-phase test, step 4. 4. Determine ara-C effect (see tables 2 and 3).

Peripheral blood lymphocytes

1. Prepare RPMI 1640 medium with 15% fetal bovine serum, 10 gl/ml heparin and 0.1 mg/ml Gentamicin (Gibco).
2. Dispense 8 ml to sterile glass tubes (Wheaton Glass Co.; obtained from Arthur Thomas) with open-top screw caps supplied with a septum for needle insertion. These tubes are supplied to physicians for collecting blood samples.
3. Freshly drawn blood (2 ml) is added aseptically directly through each tube septum by syringe needle. These blood samples must be maintained at room temperature until processed within 24 h.
4. Centrifuge blood samples at 150 g for 9 min, and discard supernatant.
5. Resuspend cells in 20 ml of medium prepared in step 1 and transfer to a T-25 culture flask. Alternatively, the blood may be collected in a sterile vacutainer tube (Beckton-Dickenson Vacutainer Systems, USA, Rutherford, N.J.) containing powdered sodium heparin. 2 ml of the blood drawn in the vacutainer may be added to 20 ml of culture medium prepared in step 1 contained in a T-25 culture flask.
6. Warm the blood culture to 37° C. and add 0.44 ml PHA (9 mg/ml HA15, Wellcome Diagnostics) also warmed to 37° C. Gas the mixture with 10% $Co_2$ in air and incubate upright at 37° C. for 72 h.
7. At approximately 24 and 48 h invert the culture flask 5–8 times to resuspend the cells. This enhances lymphocyte proliferation.
8. At 72 h pipette out 8 ml of the supernatant without disturbing the cells at the bottom of the flask, and save the supernatant. Thoroughly mix the remaining supernatant with the cells. Using a 9 inch glass pasteur pipette fill a Wintrobe hematocrit tube (Clay Adams, a Division of Becton Dickinson, Parsippany, N.J.) to the top line and spin at 2260 g for 10 minutes. This, as well as other procedures up to fixation, should be carried out at 37° C.
9. A reading of 0.5 on the Wintrobe tube is considered standard for a 5 ml sample. Therefore, to calculate the amount of blood culture needed, use the formula 0.5 divided by the hematocrit reading multiplied by 5.

10. For an experiment, pipette the correct amount of culture as determined above (usually less than 5 ml) into a T-25 flask and add supernatant from step 8 to yield 5 ml. Equilibrate gas phase with humidified 10% $Co_2$ in air.

11. Expose cultures to fluorescent light (8 $W/m^2$ for 3 h. (For light source, see $G_2$ phase test using skin fibroblasts.)

12. Add the DNA repair inhibitor, 1β-D-arabinofuranosylcytosine (ara-C, 50 gM, Sigma) at 10 min or 30 min post exposure to approximately half of the cultures, and add colcemid (0.1 μg/ml) at 30 min post exposure for 1h or 2h to all the cultures. Equilibrate gas phase with humidified 10% $CO_2$ in air and stopper tubes.

13. Centrifuge cells in 15 ml borosilicate centrifuge tubes at 150 g for 9 minutes. Draw off the supernatant down to the pellet and add 10 ml freshly prepared 0.53% KCl. Mix and incubate for 9 minutes.

14. Spin again at 150 g for 9 minutes and draw off the clear, red supernatant down to approximately 0.75 ml. Mix this remaining supernatant with the pellet.

15. Immediately fix in cold glacial acetic acid-methanol (1:3) (kept on ice at 4° C.) adding only a few drops at first with continuous mixing. Use only a glass pipette and avoid vigorous pipetting. After the cells and hemoglobin are well dispersed add more fixative up to a final amount of 6–8 ml.

16. Store in an ice bath (4° C.) for 30 min. Spin at 150 g for 9 minutes and remove supernatant. Add a drop or two of fresh fixative, resuspend pellet and bring up to 5 ml. Store in refrigerator at least overnight for better metaphase spreads.

17. To make the metaphase spreads, spin the tubes, withdraw the fixative and resuspend in 2 ml fresh fixative. Spin again, remove fixative and resuspend in 8–24 drops (depending on size of pellet) fresh fixative. Drop onto slides in a humid atmosphere and dry overnight at room temperature.

18. Stain slides for 4 minutes in aqueous Wright-Giemsa (3 parts) plus distilled water (125 parts). Rinse in tap water, air-dry overnight at room temperature.

19. Mount with Permount and dry at room temperature.

20. Determine ara-C effect (see table 4).

EXAMPLE 3

In a $G_1$-phase test as set forth in Example 1 of the present invention which is performed on cultured fibroblasts, the caffeine effect (mean±SE) for five normal lines tested was 0.0 (±0.7); that for two sporadic AD lines was 28.2 (±3.2); and that for three familial AD lines was 37.5 (±15.2) (see Table 1). These AD means are, respectively, many fold greater than the mean for the normal group. Evaluated another way, the lowest AD line's value of 14 was 600% greater than the highest normal value (2.0).

EXAMPLE 4

In a $G_2$-phase test as set forth in Example 2 of the present invention using fibroblast lines, the mean (±SE) ara-C effect for five normal lines was 29.3 (±4.8), the value for a sporadic AD line was 3.0, and the mean for four familial AD lines was 2.4 (±0.7) (see Table 2). Thus, the mean value for the normal group was 880% greater than that for the sporadic AD line and 1120% greater than the mean for the group of four familial AD lines.

EXAMPLE 5

All Down syndrome (DS) patients eventually develop AD in adulthood. Therefore, results of a $G_2$-phase test as set forth in Example 2 of the present invention on fibroblast lines from two young DS patients (13 and 14 years old) and from two normal persons (both 13 years old), closely age-matched to the DS patients, were included. The mean (±SE) ara-C effect for the two normal lines was 34.5 (±1.5), and that for the two DS lines was 2.5 (±0.5) (see Table 3). Thus, the mean ara-C effect for the normal lines was 1280% greater than that for the DS lines, indicating that the $G_2$-phase test of the invention can discriminate between normal lines and lines from individuals who do not yet have clinical evidence of AD but who are destined to develop it in later years (P=0.002).

EXAMPLE 6

In the $G_2$-phase test as set forth in Example 2 of the present invention in which PHA-stimulated peripheral blood lymphocytes are exposed to fluorescent light, the age range of the normal donors encompassed that of 19 of the 21 patients and had no relation to the results (Table 4). With either fluorescent light or ara-C alone, the CAI values (i.e., the total number of chromatid breaks plus gaps per 100 metaphase cells) of lymphocytes from the normal and patient donors were all low ($\leq 9$). However, when cells from 12 of the 13 normal donors were treated with fluorescent light followed by ara-C, their CAI values were high (mean, 31.0; range, 22–52), resulting in correspondingly high ara-C effects (mean, 29.3; range, 22–48). In contrast, when lymphocytes from all 21 patients were treated with FL followed by ara-C, their ara-C effects were $\leq 11$ (mean, 3.4; range, 2–11). Only normal donor no. 19 showed a low ara-C effect; interestingly, her fibroblast $G_1$ test on cells obtained years earlier was inconclusive (data not shown) and her fibroblast $G_2$ test showed an ara-C effect of only 2.

EXAMPLE 7

Table 5 show experimental data involving fluorescent light exposure during $G_1$-phase with and without caffeine posttreatment on skin fibroblasts from ten "normal" individuals, two "sporadic AD" individuals, four "familial AD" individuals, two individuals predetermined to develop AD because of Down syndrome (DS). While the AD cell lines were derived from patients with clinical symptoms of sporadic or familial AD, the two DS cell lines were derived from patients not reported to have clinical signs or symptoms of AD.

All cell lines were obtained from the Coriell Institute for Medical Research (Camden, N.J.). Lines with the prefix designations 'GM' and 'AG' were from the institute's NIGMS Human Genetic Mutant Cell Repository and its NIA Aging Cell Repository, respectively. The suffix A, B, or C appended to a designation indicates an expansion of the original culture.

The cells were cultured and prepared for irradiation in the same manner as were the cells described in the specification, but with 15% fetal bovine serum (FBS) instead of 10% FBS. Cells were irradiated in a 37° C. walk-in incubator directly through the glass of acid-cleaned Leighton culture tubes or the plastic of the T-25 flasks with a desk lamp fitted with two cool-white 15 W fluorescent Westinghouse bulbs (F15 T8-CW).

For the $G_1$-phase test, cultures were exposed for 5 hours at a distance yielding an intensity of 5 $W/m^2$ at the growth surface. Cultures not receiving radiation were shielded from the light by aluminum foil wrapping.

Half of the cultures received caffeine (Sigma, St. Louis, Mo.) at a final concentration of 0.25 mM for 15 hours, during the last hour of which colcemid (0.1 μg/ml; Gibco, Grand Island, N.Y.) was added to all cultures. All these procedures were performed in the incubator; however, the cultures receiving caffeine were positioned on 37° C. water bottles and briefly removed from the incubator for gassing with humidified 10% $CO_2$ in air immediately after addition of the caffeine.

At the end of the 15-hour period, the cells were treated with hypotonic solution, fixed, and stained as described in the specification.

All preparations were coded and examined blind for chromatid breaks and gaps. The proportions of cells with one or more aberrations were compared using the t-test after taking the square root transformation.

The data in the left hand columns of Table 5 indicate that, when exposed to fluorescent light during $G_1$ phase, skin fibroblasts from patients with AD (4 familial and 2 sporadic) and DS (2 trisomy 21) did not have significantly higher frequencies of chromatid breaks and gaps as compared to fibroblasts from 10 age-matched normal controls. However, addition of caffeine following $G_1$ light exposure significantly increased frequencies of chromatid aberrations in AD and DS cells as compared to cells from the normal controls: in the 10 normal lines the caffeine effect (i.e., the caffeine-induced increase in breaks and gaps combined) never exceeded 2.0 and averaged 0.3±0.4 per 100 cells in contrast to increases ranging from 14.0 to 66.0 in the AD and DS cells and averaging 36.0±6.1 for all 8 AD and DS patient lines.

In other words, the $G_1$ test accurately distinguished every normal from every patient line in the 25 caffeine experiments performed: in each of the 14 tests performed on ten normal lines the caffeine effect varied between -2.5 and +2 chromatid aberrations/100 metaphase cells, i.e., there was no effect of caffeine (Table 5). In each of the 11 tests with the patient lines the chromatid aberrations were markedly elevated (>14.0) (Table 5). The difference in response between the 10 normal lines and the 8 patient lines with regard to the caffeine effect in Table 5 is statistically significant ($P<0.05$), with no overlap of individual values. The fact that cells taken from 2 DS patients when they were 14 and 27 years of age (i.e., before they would likely have developed the neuropathology and the signs and symptoms of AD) give results similar to those of clinically affected AD individuals demonstrates that the $G_1$-phase test of the present invention can be used to predict which patients at risk will develop AD. (The inventors have determined that the probability that both of these DS cell lines tested positive for AD in $G_1$-phase test because they came from DS patients who already had the neuropathology of AD is less than 5 in 100 (data not shown)).

EXAMPLE 8

The data in the right-hand columns of Table 5 supplements the data of Table 3 and show the results of the $G_2$-phase test on skin fibroblasts from ten "normal" individuals, one "sporadic AD" individual, six "familial AD" individuals, and three individuals (including the two reported on in Table 3) predetermined to develop AD because of Down syndrome (DS). While the AD cell lines were derived from patients with clinical symptoms of sporadic or familial AD, the three DS cell lines were derived from patients not reported to have clinical signs or symptoms of AD.

All cell lines were obtained from the Coriell Institute for Medical Research (Camden, N.J.). Lines with the prefix designations 'GM' and 'AG' were from the institute's NIGMS Human Genetic Mutant Cell Repository and its NIA Aging Cell Repository, respectively. The suffix A, B, or C appended to a designation indicates an expansion of the original culture.

The cells were cultured and prepared for irradiation as described in Example 7 above.

For the $G_2$-phase test, unless noted otherwise in the footnotes of Table 5, cells were exposed for 3 hours to fluorescent light from two desk lamps to yield an intensity of 8 $W/m^2$ at the growth surface, and ara-C (Sigma) was added at a final concentration of 50 μM to half the cultures 10 min after irradiation. Twenty minutes thereafter, colcemid was added to all cultures, after which they were briefly removed from the walk-in incubator on 37° C. hot-water bottles for gassing.

After two hours in the colcemid, the cells were treated with the hypotonic solution, fixed and stained.

All preparations were coded and examined blind for chromatid breaks and gaps. The proportions of cells with one or more aberrations were compared using the t-test after taking the square root transformation.

The results, as set forth in Table 5, indicate that, when exposed to fluorescent light during the $G_2$ phase, skin fibroblasts from the group of 6 familial AD lines and the group of 3 DS lines had frequencies of chromatid breaks and gaps which did not differ significantly from those of fibroblasts from the group of 10 lines from the age-matched normal controls. Addition of ara-C resulted in an ara-C effect of 32.5±2.3 for the group of 10 normal lines, 4.7±2.0 for the group of 6 familial AD lines, and 2.0±0.6 for the group of 3 DS lines. These ara-C effects for the familial AD group and for the DS group were each significantly less than the ara-C effect of the normal group ($P<0.05$). Furthermore, the ara-C effects ranged from 19.0 to 41.0 for the individual normal lines, from 1.5 to 14.5 for the individual familial AD lines, and from 1 to 3 for the individual DS lines. Thus, there was no overlap between any normal line and any of these 9 patient lines with regard to the ara-C effect.

As shown in Table 5, it should be noted that discrepant results in the $G_2$-phase test were obtained with 1 normal and 2 AD lines: in the first experiment with normal line AG 7663A, the ara-C effect was only 2 (8–6), but in the second experiment (conducted on another culture received from the cell repository), the ara-C effect was 36 (38–2), characteristic of normal lines; in the first experiment with familial AD line AG 7613A, the ara-C effect was 27 (33–6); and in the first 2 experiments with sporadic AD line AG 6205C (an expansion line from AG 6205), the ara-C effects were 33 (36–3) and 32 (33–1). However, in an additional experiment on line AG 7613A and line AG 6205C in which ara-C was added for 1 hour (instead of the usual 2 hours and 20 min) at 30 min (instead of at the usual 10 min) after the end of irradiation, and colcemid was added for 1 hour (instead of the usual 2 hours) at 30 min after the end of irradiation, ara-C effects of 2 (10–8) and 1 (7–6), characteristic of AD lines, were obtained for familial AD line AG 7613A and for sporadic AD line 6205C, respectively. These results suggest that the discrepant results with lines AG 7613A and AG 6205C may have been due to a shorter $G_2$ phase in these cell lines, enabling some cells irradiated in S phase to enter metaphase and be evaluated cytogenetically. (Note that these 2 AD lines behaved as expected for AD cells in the Gl-phase test (See Table 5)). By shortening the time for colcemid from 2 to 1 hours, only cells irradiated in the $G_2$ phase may have been evaluated cytogenetically by ending the experiment before cells irradiated in S phase could reach metaphase.

In all, 29 G2 tests with ara-C were performed on 20 donors; only four results were unexpected, and these were matched by expected results in repeat tests.

The fact that cells taken from 3 DS patients when they were 13, 14 and 27 years of age (i.e., before they likely would have developed the neuropathology and the clinical signs and symptoms of AD) give results similar to those of clinically affected AD individuals demonstrates that the $G_2$-phase test of the present invention can be used to predict which patients at risk will develop AD. (The inventors have determined that the probability that all 3 of these DS cell lines tested positive for AD in the $G_2$-phase test because they came from DS patients who already had the neuropathology of AD is less than 1 in 100 (data not shown)).

FIG. 2 shows that caffeine and ara-C expose a DNA-repair defect in fluorescent light-irradiated fibroblast lines from patients with, or with impending, neuropathology of AD. Data presented summarize Table 5 as follows: the caffeine and ara-C effects for the 10 normal donors are, respectively, the means shown in Table 5 for the normal groups in the $G_1$- and $G_2$-phase tests; the caffeine effect for the eight patient lines is the mean calculated from the individual caffeine effects for the four FAD, two sporadic AD, and two DS patients studied in the $G_1$-phase test; the ara-C effect for the 10 patient lines is the mean calculated from the individual ara-C effects for the six FAD, one sporadic AD, and three DS patients studied in the $G_2$-phase test. Because two cell-line expansions were studied for sporadic AD donor No. 2 in the $G_1$-phase test and in the $G_2$-phase test, the average caffeine or ara-C effect for the two expansions was used. Details concerning culturing cells, $G_1$- and $G_2$-phase tests, and actions of caffeine and ara-C are presented in Table 5, FIG. 1, and the text. Error bars, ±1 SEM.

EXAMPLE 9

In the study set forth above in Example 7 (and Table 5), only three members of a Canadian AD family were evaluated in the $G_1$-phase test (FAD donor No. 1 is not in this family). Therefore, experiments were initiated to see if an elevated CAI (i.e., the total number of chromatid breaks plus gaps for the 100 metaphase cells) in the presence of caffeine was present in lines from the seven other affected members of this family whose fibroblast lines were available. Cell lines from some of the asymptomatic children, each of whom has a 50% risk for AD were also tested, partly because results with three DS patients (Table 5), who were only 13, 14 and 27 years of age at time of biopsy, indicated that the tests detected their DNA-repair abnormality in fibroblasts from skin biopsies taken before the neuropathology of AD was present.

To study the relatively large number of cell lines required for this experiment within a reasonable length of time, efforts were economized by adding caffeine to all irradiated cultures and not setting up cultures without caffeine. The lines from one normal donor (No. 5) and one FAD donor (No. 2) were also tested with this protocol; the latter line was chosen because the only Gi-test experiment in which it was studied had been conducted in plastic flasks rather than in glass Leighton culture tubes and had given the lowest CAI with caffeine of all the patient lines (Table 5). In the Leighton tube the CAI with caffeine for FAD donor No. 2 was 48 (Table 6), well up in the range given previously by the other patients' lines, all of which had been studied in Leighton tubes (Table 5).

Lines from seven additional AD patients in the Canadian family (FAD donor Nos. 3, 5, 7–11) all gave the typical high CAI values with caffeine expected for AD lines. It should be noted also that the skin biopsies from FAD donor Nos. 9–11, obtained years before the donors became symptomatic, gave the high CAI values characteristic for AD, further documenting both the presence of the DNA-repair defect prior to neurologic symptoms and the presymtomatic diagnostic value of the test.

Lines from 11 asymptomatic sons and daughters of some of the ten symptomatic Canadian patients (Table 6) were also studied. Each of these offspring is still asymptomatic and at a 50% risk of having inherited the disease-producing AD gene in this family. Of these 11 donors, eight had CAI values with caffeine well in the range given by patients with AD. The inventors predict that these eight donors will eventually become symptomatic. Seven of these eight donors were less than 32 years of age at the time of skin biopsy, suggesting that inheritance of the abnormal AD gene is manifested in the $G_1$-phase test in cells obtained at least two decades before the age of 52 years at which the disease typically produces symptoms in this family. Of the three at-risk donors who had low CAI values in the presence of caffeine, No. 10 died of cancer at the age of 49 years, and an autopsy of her brain showed no evidence of the neuropathology of AD, indicating, therefore, that she had probably not inherited the disease-producing gene. The inventors predict that the two other at-risk donors (Nos. 4 and 9), who also had low CAI values, have not inherited the defective gene and will, therefore, not develop AD.

Six additional normal lines chosen for study (Nos. 12–17, Table 6) were from donors whose ages at skin biopsy were essentially the same as those for the younger at-risk donors: approximately 15 through 30 years of age. Normal donor Nos. 12–15 gave the characteristically low CAI of normal cells. However, normal donor No. 17 twice gave high CAI values characteristic of AD cells and may, therefore, ultimately develop AD. One would expect to find some presymptomatic sporadic AD patients in any group of normal donors. The results for normal donor No. 16 are not definitive, since it is unknown which of the two discrepant values obtained is spurious. Summarizing the results of the $G_1$ test on the 16 normal donor lines tested, at least 14 donors had CAI values below those characteristically obtained with AD cells.

EXAMPLE 10

In a $G_1$-phase test with peripheral blood lymphocytes exposed to fluorescent light as set forth in Example 1, PHA stimulated T-25 lymphocyte cultures were irradiated at 48 h for 5 h at 8 W/m². Immediately thereafter, caffeine was added (final Conc., 2 mM), and 18 h later colcemid was added for 1 h. The cells were then processed for metaphase analysis as described in step 17 of Example 2 and in Sanford, K. K. et al., (1990) *J. Natl. Cancer Inst.* 82,1050–1054. Lymphocytes from the 5 sporadic AD and 3 DS donors tested had abnormally elevated CAI values when exposed to fluorescent light and then incubated with caffeine (Table 7).

General Comments

The fact that there are defects in DNA repair in many different diseases, such as the various types of cancers, does not mean that the defects are due to the same mechanism or gene nor does it mean that the DNA repair defects of cells from individuals with these other diseases would give the same results in the $G_1$- and $G_2$-phase tests as cells from individuals who either have AD or who are destined to develop AD. In fact, this is statistically unlikely. If the basis of the distinction between normal and AD cells was another genetic defect not associated with AD, then one would expect that some of the normals would have this defect and that some of the AD and DS individuals would not have this defect and that there would not be a statistically significant difference in the $G_1$- and $G_2$-phase tests of the present invention between cells from normal individuals as compared to cells from those who either have AD or are destined to develop AD. Instead, there is a statistically significant difference ($P<0.05$) between cells from normal individuals as compared to cells from those who either have AD or are destined to develop AD in the $G_1$- and $G_2$-phase tests of the present invention.

Furthermore, cells from individuals with different diseases with defects in DNA repair, such as cells from individuals with various cancers, behave differently from AD cells when used in the $G_2$-phase test assay of the prior art. For example, cells from individuals with cancer have a marked increase in total chromatid breaks and gaps as compared to normal cells when irradiated with either X-rays or fluorescent light in G2-phase without the addition of a DNA repair inhibitor such as ara-C (see, Sanford et al., U.S. Pat. No. 4,933,274, col. 1, lines 37–49), whereas cells from individuals with AD behave like normal cells when subjected to the same conditions. See Tables 1 and 5 for results concerning the use of fluorescent light on AD and normal cells. Rather, cells from individuals with AD differ from those of normal individuals only when ara-C is added, as taught in the present specification. Therefore, the effect of X-ray or fluorescent light irradiation in $G_2$-phase is quite different on cells from individuals with cancer as compared to cells from individuals with AD. Thus, the mechanism and/or gene responsible for DNA repair defects in cells from individuals with cancer is different from that in cells from individuals with AD and, in any event, cells from individuals with cancer can be distinguished from cells from individuals with AD.

Precautions and Comments

In a recent experiment analogous to that summarized in Example 4 and Table 2 (involving the $G_2$-phase test on skin fibroblasts) which was conducted on three fibroblast cell lines (data not shown), a presumed normal female gave an AD phenotype and a male with autopsy-proven AD gave a normal phenotype. The result obtained for the female may be reconcilable with a misidentification (i.e., mixup) of the cell line or with what is known about the development of AD, i.e., that it is expected that at least 5–10% of presumed normal people will develop AD. In other words, while she is presumed normal, there is at least a 5–10% chance that she is not. The results obtained for the male are more problematic, in that it was obtained from an expansion (cell line AG 6205C) of a cell line (cell line AG 6205) which gave an AD phenotype in the experiment reported in Example 4 of Table 2. Three possible explanations arise: (1) chromosomal changes may have occurred in the cell line between the time of the first test (when the original cell line was used) and the time of the recent experiment (in which an expansion of the cell line was used) which resulted in a change that caused the cell line to give a normal phenotype as opposed to an AD phenotype (the catalog from the cell repository indicates that chromosomal changes had already occurred in the AG 6205 line, which was a mosaic; thus, these changes may have increased or been selected for in the expansion); (2) the cell line used in the recent study was misidentified and actually comes from a clinically diagnosed male without AD; or (3) in the recent study some technical variation from the experimental protocol may have occurred without the inventors' knowledge. Experiments are currently being conducted to determine which of the above is correct.

Recent experiments involving the $G_2$-phase test using peripheral blood (data not shown) gave some inconsistent results, as discussed below. In one experiment, a presumed normal individual gave an AD result, and an individual with presumed sporadic AD (diagnosed clinically) gave a normal result. It is believed that the inconsistency in the presumed normal individual may be due to the use of medications (e.g., β-blockers and niacin in the presumed normal male who had previously apparently tested normal). In previous experiments involving an Italian family with familial AD inconsistent results were also obtained. It is believed that these inconsistencies may be due either to air freight shipment of the blood to the inventors' laboratory and/or to the relatively long delay in getting the blood to the laboratory (e.g., approximately 24 hours rather than the usual few hours used for the blood reported in Example 6 and Table 4).

To ensure accuracy and reproducibility of results in the present process:

1. Cultures must at all times be free of bacteria.
2. The temperature of cultures must be maintained at 37° C. up until time of fixation. A walk-in incubator room for 37° C. is recommended.
3. The pH of cultures must be maintained at physiological level (~7.2).
4. The serum lots should be pre-screened to ensure adequate DNA repair.
5. Coding of the samples should be done at each stage of the process to reduce the chance of investigator bias. For example, the person obtaining the cell cultures or blood samples should code them for the person performing the irradiating and subsequent steps and the latter person should re-code them for the person counting the chromatid breaks and gaps. However, caution must be taken to keep accurate records to avoid mixing up the samples.
6. When conducting experiments using fibroblast cell lines, it is preferable to work from an early expansion of a cell line since the possibility exists that the use of later expansions may be problematic.
7. When conducting experiments using peripheral blood, it is preferable to use blood collected within a few hours of conducting the experiment, since it is possible that longer times between the time of collection and time of conducting the experiment may have adverse effects. It is also preferable that the patient from whom the blood is collected not be on any medication, especially medication which may interfere with the generation of and/or half-life of free radicals. It is possible that such medications could cause AD cells to appear normal, or normal cells to appear like AD cells, in the $G_2$-phase test of the invention when peripheral blood is used. Collection time and medication are not expected to be problems when lymphoblastoid or culture cell lines are used.

TABLE 1

$G_1$-phase test using fibroblast lines from normal donors and from patients with sporadic or familial AD.

| Cell line[b] | Age[c]/Sex[d] | Chromatid damage expressed as (breaks + gaps)/100 cells[a] | | |
|---|---|---|---|---|
| | | No caffeine | Caffeine | Caffeine effect[e] |
| Normal | | | | |
| RB 4087 | 55/F | 13.0 | 13.0 | 0.0 |
| AG 4148 | 56/M | 10.5 (15, 6[f]) | 10.5 (15, 6[f]) | 0.0 |
| RB 4436 | 57/F | 13.5 (17, 10) | 14.0 (15, 13) | +0.5 |
| RB 4492 | 69/M | 18.0 | 15.5 (19, 12) | −2.5 |
| AG 5192 | 55/M | 8.0[f] | 10.0[f] | +2.0 |
| | Mean (±SE): | 12.6 (±1.7) | 12.6 (±1.0) | 0.0 (±0.7) |
| Sporadic AD | | | | |
| AG 6205[g] | 67/M | 9.0 | 34.0 | +25.0 |

TABLE 1-continued

G$_1$-phase test using fibroblast lines from normal donors and from patients with sporadic or familial AD.

| Cell line[b] | Age[c]/Sex[d] | Chromatid damage expressed as (breaks + gaps)/100 cells[a] | | |
|---|---|---|---|---|
| | | No caffeine | Caffeine | Caffeine effect[e] |
| AG 6869[g] | 60/F | 9.0 | 40.5 (41, 40) | +31.5 |
| | Mean (±SE): | 9.0 (±0.0) | 37.2 (±3.2) | +28.2 (±3.2) |
| | P-value[h]: | 0.25 | 3 × 10$^{-4}$ | 4 × 10$^{-5}$ |
| Familial AD[i] | | | | |
| AG 4159[j] | 58/F | 13.0 (16, 10) | 45.5 (44, 47) | +32.0 |
| AG 4401[g] | 53/F | 16.0 | 82.0 | +66.0 |
| AG 6848A[g,k] | 56/F | 8.0[f] | 22.0[f] | +14.0 |
| | Mean (±SE): | 12.3 (±2.3) | 49.8 (±17.5) | ±37.5(±15.2) |
| | P-value[h]: | 0.92 | 0.013 | 0.015 |

[a]Values outside of parentheses are the results of either the single experiment performed (rounded off to nearest whole number) or the average result of the multiple experiments performed whose individual results (rounded off to the nearest whole number) are shown in parentheses. Values shown are from experiments using Leighton culture tubes, unless noted otherwise.
[b]All cell lines were obtained from the Coriell Institute for Medical Research, 401 Haddon Avenue, Camden, NJ 08103. Additional information on the lines designated AG is presented in the National Institute on Aging 1991 Catalog of Cell lines available from the Coriell Institute for Medical Research. The four-digit designation for both the AG and RB lines has recently been increased to five digits by placing a zero prior to the original first digit (e.g., RB 4087 has become RB 04087).
[c]Age of donor in years at time of skin biopsy.
[d]F, female; M, male.
[e]Value in the presence of caffeine less value in its absence. The greater than normal caffeine effect for the sporadic and familial AD lines is due to increase in both breaks and gaps.
[f]Experiment conducted in T-25 culture flask instead of in a Leighton culture tube.
[g]From a patient whose clinical diagnosis of AD has been confirmed on autopsy or by brain biopsy.
[h]Two-sided P-value for comparison to mean of normal group.
[i]The two familial AD lines AG 4159 and AG 6848A are from the Canadian family which manifests a dominantly inherited form of autopsy-proven AD. The family pedigree is presented in the National Institute on Aging 1991 Catalog of Cell Lines.
[j]This line is from a patient whose mother had the familial form of AD and whose father had a sporadic form of AD. The patient manifested the early clinical onset typical of the familial form in this family, and she is, therefore, classified as having familial AD. She is the donor of lymphoblastoid cell line AG 4160B in Table 5.
[k]The donor of this fibroblast line is the donor of lymphoblastoid cell line AG 6849A in Table 5.

TABLE 2

G$_2$-phase test using fibroblast lines from normal donors and from patients with sporadic or familial AD.

| Cell line[b] | Age[c]/Sex[d] | Chromatid damage expressed as (breaks + gaps)/100 cells[a] | | |
|---|---|---|---|---|
| | | No ara-C | Ara-C | Ara-C effect[e] |
| Normal | | | | |
| RB 4087 | 55/F | 4.0 | 44.0 | +40.0 |
| AG 4148 | 56/M | 14.5 (13, 16) | 32.0 | +17.5 |
| RB 4436 | 57/F | 8.0 | 30.0 | +22.0 |
| RB 4492 | 69/M | 2.0 | 43.0 | +41.0 |
| AG 5192 | 55/M | 6.0[f] | 32.0[f] | +26.0 |
| | Mean (±SE): | 6.5 (±2.1) | 36.2 (13.0) | 29.3 (14.8) |
| Sporadic AD | | | | |
| AG 6205[a] | 67/M | 6.0 | 9.0 (10, 8) | +3.0 |
| | P-value[h]: | 0.92 | 0.008 | 0.029 |

TABLE 2-continued

G$_2$-phase test using fibroblast lines from normal donors and from patients with sporadic or familial AD.

| Cell line[b] | Age[c]/Sex[d] | Chromatid damage expressed as (breaks + gaps)/100 cells[a] | | |
|---|---|---|---|---|
| | | No ara-C | Ara-C | Ara-C effect[e] |
| Familial AD[i] | | | | |
| AG 4159[j] | 58/F | 5.0 | 8.0 | +3.0 |
| AG 4401[g] | 53/F | 11.5 (7, 15) | 12.0 | +0.5 |
| AG 6844B[g] | 59/M | 3.0 | 7.0 | +4.0 |
| AG 6848A[g,k] | 56/F | 8.0[f] | 10.0[f] | +2.0 |
| | Mean (±SE): | 6.9 (±1.9) | 9.2 (±1.1) | +2.4 (±0.7) |
| | P-value[h]: | 0.94 | 4 × 10$^{-5}$ | 2 × 10$^{-4}$ |

[a]Values outside of parentheses are the results of either the single experiment performed (rounded off to nearest whole number) or the average result of the multiple experiments performed whose individual results (rounded off to the nearest whole number) are shown in parentheses. Values shown are from experiments using Leighton culture tubes, unless noted otherwise.
[b]All cell lines were obtained from the Coriell Institute for Medical Research, 401 Haddon Avenue, Camden, NJ 08103. Additional information on the lines designated AG is presented in the National Institute on Aging 1991 Catalog of Cell lines available from the Coriell Institute for Medical Research. The four-digit designation for both the AG and RB lines has recently been increased to five digits by placing a zero prior to the original first digit (e.g., RB 4087 has become RB 04087).
[c]Age of donor in years at time of skin biopsy.
[d]F, female; M, male.
[e]Value in the presence of ara-C less value in its absence. The greater ara-C effect for the normal lines as compared to that for the sporadic and familial AD lines is due to increase in both breaks and gaps.
[f]Experiment conducted in T-25 culture flask instead of in a Leighton culture tube.
[g]From a patient whose clinical diagnosis of AD has been confirmed on autopsy or by brain biopsy.
[h]Two-sided P-value for comparison to mean of normal group.
[i]The two familial AD lines AG 4159, AG 6844B, and Ag 6848A are from the Canadian family which manifests a dominantly inherited form of autopsy-proven AD. The family pedigree is presented in the National Institute on Aging 1991 Catalog of Cell Lines.
[j]This line is from a patient whose mother had the familial form of AD and whose father had a sporadic form of AD. The patient manifested the early clinical onset typical of the familial form in this family, and she is, therefore, classified as having familial AD. She is the donor of lymphoblastoid cell line AG 4160B in Table 5.
[k]The donor of this fibroblast line is the donor of lymphoblastoid cell line AG 6849A in Table 5.

TABLE 3

G$_2$-phase test using fibroblast lines from normal donors and from patients with sporadic or familial AD.

| Cell line[b] | Age[c]/Sex[d] | Chromatid damage expressed as (breaks + gaps)/100 cells[a] | | |
|---|---|---|---|---|
| | | No ara-C | Ara-C | Ara-C effect[e] |
| Normal | | | | |
| GM 1651A | 13/F | 10.0 | 46.0 | +36.0 |
| GM 2037B | 13/M | 7.0 | 40.0 | +33.0 |
| | Mean (+SE): | 8.5 (±1.5) | 43.0 (±3.0) | +34.5 (±1.5) |
| Down syndrome | | | | |
| GM 0201A | 13/F | 8.0 | 11.0 | +3.0 |
| GM 2767C | 14/F | 7.0 | 9.0 | +2.0 |
| | Mean (±SE): | 7.5 (±0.5) | 10.0 (±1.0) | +2.5 (±0.5) |
| | P-value[f]: | 0.60 | 0.007 | 0.002 |

[a]Each value is the result of a single experiment and has been rounded off to the nearest whole number. Values shown are from experiments using Leighton culture tubes.

TABLE 3-continued

G$_2$-phase test using fibroblast lines from normal donors and from patients with sporadic or familial AD.

| | | Chromatid damage expressed as (breaks + gaps)/100 cells[a] | | |
|---|---|---|---|---|
| Cell line[b] | Age[c]/Sex[d] | No ara-C | Ara-C | Ara-C effect[e] |

[b]All cell lines were obtained from the Coriell Institute for Medical Research, 401 Haddon Avenue, Camden, NJ 08103. Additional information on the lines is presented in the National Institute of General Medical Sciences' 1990/1991 Catalog of Cell lines of the NIGMS Human Genetic Mutant Cell Repository available from the Coriell Institute for Medical Research. The four-digit designation for lines has recently been increased to five digits by placing a zero prior to the original first digit (e.g., GM 1651A has become GM 01651A).
[c]Age of donor in years at time of skin biopsy.
[d]F, female; M, male.
[e]Value in the presence of ara-C less value in its absence. The greater ara-C effect for the normal lines compared to that for the Down Syndrome lines is due to increase in both breaks and gaps.
[f]Two-sided P-value for comparison to mean of normal group.

TABLE 4

G$_2$-test data using PHA-stimulated lymphocytes

| | | | CAI | | |
|---|---|---|---|---|---|
| Donor no. | Age, yr | Sex | Light alone | Light and ara-C | Ara-C effect |
| | | | Normal | | |
| 19 | >70 | W | 2 | 2 | 0 |
| 20 | 30 | M | 2 | 24 | 22 |
| 21 | 31 | M | 0 | 24 | 24 |
| 22 | 35 | M | 0 | 22 | 22 |
| 23 | 42 | M | 1† | 27† | 26 |
| 24 | 51 | F | NT | 28 | ≦28 |
| 25 | 52 | M | 0 | 24 | 24 |
| 26 | 52 | M | 3† | 47† | 44 |
| 27 | 60 | M | 0† | 26† | 26 |
| 28 | 62 | M | 5 | 44 | 39 |
| 29 | 63 | F | 2 | 26 | 24 |
| 30 | 76 | F | 4 | 52 | 48 |
| 31 | 32 | F | 2 | 28 | 26 |
| | | | Familial AD (Canadian) | | |
| 3‡ | 63 | F | 6 | 12 | 6 |
| | | | (Italian) | | |
| 12 | 40 | M | 2† | 13† | 11 |
| 13 | 46 | M | 0 | 2 | 2 |
| 14 | 47 | F | 9† | 14†§ | 5 |
| 15 | 50 | M | 3† | 9† | 6 |
| | | | (German) | | |
| 16 | 49 | M | 8 | 10§ | 2 |
| | | | Sporadic AD | | |
| 1‡ | 68 | F | 2 | 4§ | 2 |
| 3 | 51 | M | 6 | 8§ | 2 |
| 4 | 56 | M | 6 | 6 | 0 |
| 5 | 74 | F | 6 | 10 | 4 |
| 6 | 74 | M | 0 | 6 | 6 |
| 7¶ | 81 | M | 1† | 4† | 3 |
| 8 | 84 | F | 6 | 8§ | 2 |
| 9 | 75 | F | 0 | 2 | 2 |
| | | | DS | | |
| 3 | 36 | M | NT | 6 | ≦6 |
| 4 | 40 | M | 4 | 6 | 2 |
| 5 | 44 | F | 2† | 3† | 1 |
| 6 | 56 | M | 0 | 3† | 3 |
| 7 | 57 | F | 2 | 3† | 1 |
| 8 | 62 | F | 1† | 1† | 0 |
| 9 | 66 | M | NT | 4 | ≦4 |

(footnote to Table 4)

Age, age at venipuncture; NT, not tested; ara-C effect, see Table 1. The initial experiment on familial AD donor 16 was performed with that on normal donor 27; the patient gave a high, and the normal donor a low, ara-C effect. Suspecting a mixup, a repeat blood drawing on familial AD donor 16 gave the results shown; 2 repeat experiments on normal donor 27 gave CA frequencies for light plus ara-C of 22 and 30, and the averages of these repeat experiments are the results shown.
*G$_1$-test results for this donor were inconclusive (data not shown).
†Mean of 2–4 experiments.
‡G$_1$-test results for this donor (i.e., AG 6869) are in Table 5.
§Ara-C added at 10 min postirradiation.
¶Of his 8 siblings, 1 may have a problem (of unknown etiology) with memory and judgment.

TABLE 5

Chromatid Aberration Data From Individual $G_1$- and $G_2$- phase tests. The CAI, chromatid aberration index, is the total number of chromatid breaks plus gaps for the 100 metaphase cells examined; for experiments in which <100 but at least 50 metaphase cells were available for evaluation, the CAI was calculated per 100 cells; if <50 metaphase cells were available for evaluation, the results were discarded. When duplicate or triplicate experiments were performed on a cell line, the replicate experiments' CAI values are shown in parentheses, and the average CAI for the replicate experiments is shown outside the parentheses; the first, second, and third entries in parentheses shown for a cell line in the absence of a DNA-repair inhibitor were obtained from the same experiments, respectively, as the first, second, and third entries in parentheses for that cell line in the presence of the DNA-repair inhibitor. Ara-C, 1-β-D-arabinofuranosylcytosine; NT, not tested.

| Fibroblast cell line | Donor Age at biopsy[a] (yrs) | Sex | $G_1$-phase test CAI No caffeine | Caffeine | Caffeine effect[b] | $G_2$-phase test CAI No ara-C | Ara-C | Ara-C effect[c] |
|---|---|---|---|---|---|---|---|---|
| Normal | | | | | | | | |
| 1. GM 0409A | 7 | M | 12.0[d] | 12.0 | 0.0 | NT | NT | NT |
| 2. GM 1864A | 11 | M | 2.0[d] | 3.0 | 1.0 | 2.0[d] | 43.0[d] | 41.0 |
| 3. GM 1651A | 13 | F | 6.0 | 7.0 | 1.0 | 10.0 | 46.0[d] | 36.0 |
| 4. GM 2037[e] | 13 | M | 11.0 | 13.0[d] | 2.0 | 7.0 | 40.0 | 33.0 |
| 5. GM 2912A | 26 | M | 11.0 | 10.0 | −1.0 | 8.0 | 41.0[d] | 33.0 |
| 6. RB 4087 | 55 | F | 13.0 | 13.0 | 0.0 | 4.0[d] | 44.0 | 40.0 |
| 7. AG 5192 | 55 | M | 8.0[d,f] | 10.0[d,f] | 2.0 | 4.5 (6[d,f],3) | 34.5 (32[d,f],37) | 30.0 |
| 8. AG 4148[g] | 56 | M | 8.7 (15,6[d,f],5) | 9.0 (15,6[d,f],6) | 0.3 | 10.6 (16[h],13[h],3[i]) | 35.0 (NT,32[j],38[k]) | 24.4 |
| 9. RB 4436 | 57 | F | 13.5 (17,10) | 14.0 (15,13) | 0.5 | 5.0 (8,2) | 32.5 (29,36) | 27.5 |
| 10. AG 7663A | 67 | F | NT | NT | NT | 4.0 (6,2) | 23.0 (8,38) | 19.0 |
| 11. RB 4492 | 69 | M | 18.0 (18[l],NT) | 15.5 (19[l],12) | −2.5 | 2.0 | 43.0 | 41.0 |
| | Mean ± SEM | | 10.3 ± 1.4 | 10.6 ± 1.2 | 0.3 ± 0.4 | 5.7 ± 1.0 | 38.2 ± 2.2 | 32.5 ± 23 |
| Familial AD | | | | | | | | |
| 1. AG 4401 | 53 | F | 16.0 | 82.0 | 66.0 | 10.5 (14[h],7[h]) | 12.0 (NT,12[j]) | 1.5 |
| 2. AG 6848A | 56 | F | 8.0[d,f,m] | 22.0[d,f,m] | 14.0 | 8.0[d,f] | 10.0[d,f] | 2.0 |
| 3. AG 6840A | 56 | M | NT | NT | NT | 5.0[d] | 7.0[d] | 2.0 |
| 4. AG 4159 | 58 | F | 13.0 (16,10) | 45.5 (44,47) | 32.0 | 5.0[h] | 8.0[j] | 3.0 |
| 5. AG 6844B | 59 | M | NT | NT | NT | 3.0[d] | 8.0[d] | 2.0 |
| 6. AG 7613A | 66 | M | 5.0[d] | 33.0[d] | 28.0 | 7.0 (6[d],8[d,i]) | 21.5 (33[d],10[k]) | 14.5 |
| | Mean ± SEM | | 10.5 ± 2.5 | 45.6 ± 13.0 | 35.0 ± 11.0 | 6.4 ± 1.1 | 11.1 ± 2.2 | 4.7 ± 2.0 |
| | Significance | | | n | n | | n | n |
| Sporadic AD | | | | | | | | |
| 1. AG 6869 | 60 | F | 9.0 (9[l],NT) | 40.5 (41[l],40) | 31.5 | NT | NT | NT |
| 2. AG 6205 | 67 | M | 9.0[d] | 34.0 | 25.0 | 9.0 (NT,9[d]) | 9.0 (10,8[d]) | 0.0 |
| AG 6205C | | | 3.0 | 41.0[d] | 38.0 | 3.3 (3,1,6[l]) | 25.3 (36,33,7[k]) | 22.0 |
| Down Syndrome | | | | | | | | |
| 1. GM 0201A | 13 | F | NT | NT | NT | 8.0 | 11.0 | 3.0 |
| 2. GM 2767C | 14 | F | 0.0 | 45.0 | 45.0 | 7.0 | 9.0 | 2.0 |
| 3. GM 4928A | 27 | M | 4.0[d] | 44.0 | 40.0 | 3.0[i] | 4.0[i] | 1.0 |
| | Mean ± SEM | | 2.0 ± 2.0 | 44.5 ± 0.5 | 42.5 ± 2.5 | 6.0 ± 1.5 | 8.0 ± 2.1 | 2.0 ± 0.6 |
| | Significance | | n | n | n | | n | n |

[a]All lines are known to have been derived from skin biopsies except the Down syndrome lines; the latter are presumed to have been similarly obtained.
[b]CAI with caffeine less CAI without caffeine.
[c]CAI with ara-C less CAI without ara-C.
[d]Normalized to 100 metaphase cells from results on the 50 to 97 cells evaluated.
[e]GM2037A was used in the $G_1$-phase experiment; GM 2037B in the $G_2$-phase experiment.
[f]Experiment conducted in T-25 flask.
[g]AG 4148A was used in the third $G_2$-phase experiment.
[h]Two hours of irradiation; colcemid added for 1 hour at 30 min after end of irradiation; no gassing with 10% $CO_2$.
[i]Colcemid added for 1 hour at 30 min after end of irradiation; no gassing with 10% $CO_2$.
[j]Two hours of irradiation; ara-C and colcemid added for 1 hour at 30 min after end of irradiation; no gassing with 10% $CO_2$.
[k]Ara-C and colcemid added for 1 hour at 30 min after end of irradiation; no gassing with 10% $CO_2$.
[l]In the $G_1$-phase text a mixup between male cell line RB 4492 and the concomitantly studied female AG 6869 line was corrected when the inventors determined the sex of the metaphase cells being evaluated; the results shown are correctly identified.
[m]In a prior experiment using T-25 flasks, the flask allegedly without caffeine had a CAI of 24, while the flask allegedly with caffeine had a CAI of 10; these anamolous results suggested an error had occurred in labelling the flasks with regard to the presence or absence of caffeine; the experiment was repeated and gave the results shown.
[n]Significant difference (2-sided $P < 0.05$) from normal mean.

TABLE 6

Presymptomatic diagnosis using the $G_1$-phase test. Fibroblasts were from donors at a 50% risk for AD in the Canadian family, from additional donors affected with AD in the family, and from additional normal donors age-matched to the younger at-risk donors. All cell lines were ordered from the Coriell Institute, received, and coded by J.H.R. In contrast to the experiments of Table, 1, these experiments were performed by L.M. and R.P. The cell line designation and exact age of each donor still at risk for AD and of normal donor Nos. 16 and 17 have been withheld (indicated by W) to preserve donor confidentiality. Cultures, all of which received caffeine, were prepared as described in Table 1, except for a few technical changes. Instead of adding caffeine to the cultures in the 37° C. walk-in incubator immediately after the end of irradiation, the cultures were positioned on bottles containing 37° C. water, removed from the incubator, and taken to the room-temperature laminar-flow culture hood for addition of the caffeine in a sterile atmosphere, with the result that caffeine was added to the cultures several min after the end of irradiation rather than immediately thereafter; two of the results were obtained from cultures without antibiotics; in the last two experiments performed, involving a total of five lines for which results are reported, the caffeine solution was sterilized by passage through a 0.22-micron pore-sized filter. If there was microscopic evidence of microbial contamination on any of the coverslips from the four Leighton culture tubes of a cell line in an experiment, all data on that line from that experiment were omitted from the table. Because of contamination in all tests, no results are presented for normal line AG 7663A, which had a high and a low CAI with caffeine in the only two experiments performed, and for three at-risk lines, each of whose single experiments showed a high CAI with caffeine.

| | Donor | | | |
|---|---|---|---|---|
| No. | Fibroblast cell line | Age at skin biopsy (yrs) | Sex | CAI[a] with Caffeine |
| Normal | | | | |
| 5. | GM 2912A | 26 | M | 4 |
| 12. | GM 8399 | 19 | F | 5 |
| 13. | AG 9309 | 21 | F | 3 |
| 14. | AG 6103 | 30 | M | 4 |
| 15. | AG 3651D | 25 | F | 3 |
| 16. | W | <32 | F | 19[b] (5, 33[c,d,e]) |
| 17. | W | <32 | F | 37 (38, 36[e]) |
| FAD | | | | |
| | Symptomatic before skin biopsy: | | | |
| 2. | AG 6848B | 56 | F | 48[b] |
| 3. | AG 6840A | 56 | M | 32 |
| 5. | AG 6844C | 59 | M | 43 |
| 7. | AG 7637A | 55 | F | 67[f] |
| 8. | AG 8170A | 56 | M | 40[b,c,g] |
| | Asymptomatic at skin biopsy: | | | |
| 9. | AG 7629B | 54 | M | 37[b,c] |
| 10. | AG 7671 | 43 | M | 42 (50[d], 42[d,e], 35[h]) |
| 11. | AG 8129 | 50 | M | 36[b] (40[f], 32[c,d,e]) |
| At Risk | | | | |
| 1. | W | <32 | M | 49 |
| 2. | W | <32 | F | 33[f] |
| 3. | W | <32 | F | 39 |
| 4. | W | <32 | F | 4 |
| 5. | W | <32 | F | 47 |
| 6. | W | <32 | F | 76[f] |
| 7. | W | <32 | F | 40 |
| 8. | W | <32 | F | 33 |
| 9. | W | >32 | M | 5 |
| 10. | AG 7655[i] | 47 | F | 8[b] (10[c,d], 5[c,e]) |
| 11. | W | >32 | F | 46[d] |

[a]CAI, see Table 5 for definition.
[b]These lines had some results omitted because of microbial contamination; the mean and individual CAI values for these lines, without omitting any data, are as follows: normal donor No. 16, 14 (5, 4, 33); FAD donor No. 2, 27 (48, 5); FAD donor No. 8, 17 (6, 6, 40); FAD donor No. 9, 22 (6, 37); FAD donor No. 11, 28 (40, 6, 32, 32); at-risk donor No. 10, 16 (34, 10, 5).
[c]The caffeine solution was filtered through a 0.22-micron pore-sized filter for sterilization.
[d]Fifty to 58 metaphases examined.
[e]Results using a second culture thawed and sent from the cell repository.
[f]Sixty-seven to 81 metaphases examined.
[g]In one experiment on the cell line from FAD donor No. 8, the inventors obtained metaphase preparations that differed from all others previously studied, for in a majority of the cells the chromosomes were overcondensed and not well separated by the hypotonic treatment the inventors had been routinely using; therefore, such unsatisfactory preparations can not be properly evaluated for chromatid aberrations, and the inventors consider the low CAI reading of 3 to be spurious.
[h]Results using a third culture sent from the cell repository.
[i]Died of metastatic malignant melanoma at 49 years of age with autopsy showing no evidence to support a diagnosis of AD.

TABLE 7

$G_1$-test data using FL-irradiated lymphocytes

| | | | CAI | | |
|---|---|---|---|---|---|
| Donor no. | Age, yr | Sex | Caffeine alone | FL followed by caffeine | FL effect |
| Normal | | | | | |
| 23 | 43 | M | 6 | 8 | 2 |
| 27 | 61 | M | 10 | 10 | 0 |
| Sporadic AD | | | | | |
| 3 | 55 | M | 6 | 34 | 28 |
| 7 | 81 | M | 4 | 62 | 58 |
| 9 | 75 | F | 4 | 82† | 78 |
| 10 | 71 | M | 2 | 40 | 38 |
| 11 | 86 | F | 4 | 38 | 34 |
| DS | | | | | |
| 10 | 35 | M | 4 | 46 | 42 |
| 11 | 36 | M | NT | 56 | ≤56 |
| 12 | 53 | F | NT | 46 | ≤46 ‡ |

Age, see Table 4; CAI, see header of Table 5; NT, not tested; FL effect, CAI for 'FL followed by caffeine' less that for 'caffeine alone'.

TABLE 7-continued

G₁-test data using FL-irradiated lymphocytes

|  |  |  | CAI | | |
|---|---|---|---|---|---|
| Donor no. | Age, yr | Sex | Caffeine alone | FL followed by caffeine | FL effect |

In the absence of FL and caffeine, normal donors 23 and 27, sporadic AD donor 10, and DS donor 10 had CAI values of 0, 0, 0 and 2, respectively.
†Without caffeine, the CAI value was 4.
‡Caffeine added 30 min postirradiation.

We claim:

1. A process for indicating a diagnosis of Alzheimer disease in a patient suspected of having Alzheimer disease comprising the steps of:
    a) obtaining cells from the patient;
    b) culturing the cells to obtain cell cultures wherein $G_1$-phase cells are present;
    c) irradiating with fluorescent light the cell cultures wherein $G_1$-phase cells are present to obtain irradiated cell cultures;
    d) adding caffeine to approximately half of the irradiated cell cultures;
    e) incubating the irradiated cell cultures to allow for DNA repair;
    f) arresting cell division in the irradiated cell cultures;
    g) counting chromatid breaks and chromatid gaps to determine an amount of chromatid damage in the irradiated cell cultures to which caffeine was added;
    h) counting chromatid breaks and chromatid gaps to determine an amount of chromatid damage in the irradiated cell cultures to which caffeine was not added;
    i) determining whether there is a significant increase in the amount of chromatid damage in the irradiated cell cultures to which caffeine was added as compared to the amount of chromatid damage in the irradiated cell cultures to which caffeine was not added;
wherein a significant increase in the amount of chromatid damage in the irradiated cell cultures to which caffeine was added as compared to the amount of chromatid damage in the irradiated cell cultures to which caffeine was not added indicates the diagnosis of Alzheimer disease in patients suspected of having Alzheimer disease.

2. The process of claim 1 wherein the cell cultures are irradiated for 5 hours.

3. The process of claim 1 wherein the cell cultures are subconfluent on growth surfaces while the cells cultures are irradiated.

4. The process of claim 1 wherein cell division is arrested in the cell cultures 14 to 15 hours after caffeine is added.

5. The process of claim 1 wherein the cell cultures comprise skin fibroblasts.

6. The process of claim 5 wherein 0.25 mM caffeine is added.

7. The process of claim 1 wherein the cell cultures are irradiated with fluorescent light at about 5 W/m².

8. The process of claim 1 wherein the cell cultures comprise peripheral blood lymphocytes.

9. The process of claim 8 wherein 2.0 mM caffeine is added.

10. The process of claim 8, wherein cell division is arrested in the irradiated cell cultures 18 hours after caffeine is added.

11. The process of claim 1 wherein the cell cultures are not exposed to light of wavelength <500 nm prior to or immediately after irradiating the cell cultures and are not exposed to any light of wavelength <500 nm while irradiating the cell cultures other than the fluorescent light used while irradiating the cell cultures.

12. A process for indicating a diagnosis of Alzheimer disease in a patient suspected of having Alzheimer disease comprising the steps of:
    a) obtaining cells from the patient;
    b) culturing the cells to obtain cell cultures wherein $G_2$-phase cells are present;
    c) irradiating with fluorescent light the cell cultures wherein $G_2$-phase cells are present to obtain irradiated cell cultures;
    d) adding ara-C to approximately half of the irradiated cell cultures;
    e) incubating the irradiated cell cultures to allow for DNA repair;
    f) arresting cell division in the irradiated cell cultures;
    g) counting chromatid breaks and chromatid gaps to determine an amount of chromatid damage in the irradiated cell cultures to which ara-C was added;
    h) counting chromatid breaks and chromatid gaps to determine an amount of chromatid damage in the irradiated cell cultures to which ara-C was not added; and
    i) determining whether there is an absence of a significant increase in the amount of chromatid damage in the irradiated cell cultures to which ara-C was added as compared to the amount of chromatid damage in the irradiated cell cultures to which ara-C was not added;
wherein the absence of a significant increase of at least 15 gaps plus breaks per 100 metaphase cells in the irradiated cell cultures to which ara-C was added as compared to the amount of chromatid damage in the irradiated cell cultures to which ara-C was not added indicates the diagnosis of Alzheimer disease in patients who are suspected of having Alzheimer disease.

13. The process of claim 12 wherein the cell cultures are irradiated for 3 hours.

14. The process of claim 12 wherein the cell cultures are subconfluent on growth surfaces while the cell cultures are irradiated.

15. The process of claim 12 wherein ara-C is added 10 min to 30 min after the cell cultures are irradiated.

16. The process of claim 12 wherein cell division is arrested 0.5 to 1.5 hours after the cells are irradiated.

17. The process of claim 12 wherein the cell cultures comprise skin fibroblasts or peripheral blood lymphocytes.

18. The process of claim 17 wherein 50 µM ara-C is added.

19. The process of claim 12 wherein the cell cultures are irradiated with fluorescent light at about 8 W/m².

20. The process of claim 12 wherein the cell cultures are not exposed to light of wavelength <500 nm prior to or immediately after irradiating the cell cultures and are not exposed to any light of wavelength <500 nm while irradiating the cell cultures other than the fluorescent light used while irradiating the cell cultures.

* * * * *